(12) United States Patent
Nelson et al.

(10) Patent No.: US 11,219,775 B2
(45) Date of Patent: Jan. 11, 2022

(54) RETENTION MECHANISM FOR AN IMPLANTABLE LEAD

(71) Applicant: CARDIAC PACEMAKERS, INC., St. Paul, MN (US)

(72) Inventors: Bryan Peter Nelson, Woodbury, MN (US); Christopher Alan Fuhs, Roseville, MN (US); G. Shantanu Reddy, Minneapolis, MN (US); Peter Hall, Andover, MN (US); Andrew L. De Kock, Ham Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 88 days.

(21) Appl. No.: 16/397,086

(22) Filed: Apr. 29, 2019

(65) Prior Publication Data
US 2019/0336779 A1     Nov. 7, 2019

Related U.S. Application Data

(60) Provisional application No. 62/665,216, filed on May 1, 2018.

(51) Int. Cl.
*A61N 1/39*     (2006.01)
*A61N 1/375*    (2006.01)
(Continued)

(52) U.S. Cl.
CPC ............ *A61N 1/3956* (2013.01); *A61L 31/10* (2013.01); *A61N 1/0504* (2013.01); *A61N 1/057* (2013.01);
(Continued)

(58) Field of Classification Search
CPC .... A61N 1/3956; A61N 1/057; A61N 1/0504; A61N 1/0563; A61N 1/059; A61N 1/375; A61N 2001/0582; A61L 31/10
See application file for complete search history.

(56) References Cited

U.S. PATENT DOCUMENTS 4,716,888 A     1/1988  Wesner
4,796,643 A *   1/1989  Nakazawa ............. A61N 1/057
                                                 600/375

(Continued)

FOREIGN PATENT DOCUMENTS

EP       0085967 A1     8/1983
WO     2012151356 A1    8/2012

OTHER PUBLICATIONS

Darrat et al.; "Single Incision Technique For Placement Of Subcutaneous Implantable Cardioverter Defibrillators," http://abstractsonline.com/pp8/, accessed May 14, 2018.
(Continued)

*Primary Examiner* — Carl H Layno
*Assistant Examiner* — Anh-Khoa N Dinh
(74) *Attorney, Agent, or Firm* — Seager, Tufte & Wickhem LLP

(57) ABSTRACT

Retention devices for use with an implantable medical device (IMD) are disclosed. An illustrative retention device may comprise an elongate body including a hollow lumen configured to receive a lead of the IMD and an outer surface configured to receive a suture. The retention device may also include a securing mechanism configured to push against tissue of a patient.

18 Claims, 29 Drawing Sheets

(51) Int. Cl.
*A61N 1/05* (2006.01)
*A61L 31/10* (2006.01)

(52) U.S. Cl.
CPC ............ *A61N 1/0563* (2013.01); *A61N 1/059* (2013.01); *A61N 1/375* (2013.01); *A61N 2001/058* (2013.01); *A61N 2001/0582* (2013.01)

(56) References Cited

U.S. PATENT DOCUMENTS

| | | | |
|---|---|---|---|
| 6,647,292 | B1 | 11/2003 | Bardy et al. |
| 6,721,597 | B1 | 4/2004 | Bardy et al. |
| 7,149,575 | B2 | 12/2006 | Ostroff et al. |
| 7,194,302 | B2 | 3/2007 | Bardy et al. |
| 7,493,175 | B2 | 2/2009 | Cates et al. |
| 7,655,014 | B2 | 2/2010 | Ko et al. |
| 8,019,443 | B2 | 9/2011 | Schleicher et al. |
| 8,244,377 | B1 | 8/2012 | Pianca et al. |
| 8,285,397 | B2 | 10/2012 | Grandhe |
| 8,332,043 | B1 | 12/2012 | Jaax et al. |
| 9,610,435 | B2 | 4/2017 | Schleicher et al. |
| 9,981,121 | B2 | 5/2018 | Seifert et al. |
| 2004/0230279 | A1 | 11/2004 | Cates et al. |
| 2004/0230281 | A1* | 11/2004 | Heil ............... A61N 1/3956 607/126 |
| 2004/0230282 | A1 | 11/2004 | Cates et al. |
| 2007/0255295 | A1 | 11/2007 | Starkbaum et al. |
| 2007/0293925 | A1* | 12/2007 | Zarembo ............ A61N 1/057 607/126 |
| 2008/0009914 | A1* | 1/2008 | Buysman ............ A61N 1/05 607/41 |
| 2008/0103576 | A1* | 5/2008 | Gerber ............... A61N 1/0534 607/128 |
| 2008/0183266 | A1* | 7/2008 | D'Aquanni ......... A61N 1/057 607/126 |
| 2008/0208247 | A1 | 8/2008 | Rutten et al. |
| 2009/0125059 | A1 | 5/2009 | Verzal et al. |
| 2009/0210043 | A1 | 8/2009 | Reddy |
| 2009/0248095 | A1* | 10/2009 | Schleicher ......... A61N 1/0558 607/2 |
| 2010/0131036 | A1 | 5/2010 | Geistert et al. |
| 2010/0256696 | A1 | 10/2010 | Schleicher et al. |
| 2011/0029057 | A1* | 2/2011 | Flach ............... A61N 1/057 607/122 |
| 2011/0054580 | A1 | 3/2011 | Desai et al. |
| 2011/0054581 | A1 | 3/2011 | Desai et al. |
| 2013/0131767 | A1 | 5/2013 | Desai et al. |
| 2014/0144580 | A1 | 5/2014 | Desai et al. |
| 2014/0194963 | A1 | 7/2014 | Desai et al. |
| 2014/0330248 | A1 | 11/2014 | Thompson-Nauman et al. |
| 2014/0330327 | A1 | 11/2014 | Thompson-Nauman et al. |
| 2015/0343199 | A1* | 12/2015 | Wechter ............ A61N 1/0558 607/116 |
| 2015/0352352 | A1 | 12/2015 | Soltis et al. |
| 2016/0143643 | A1 | 5/2016 | Smith et al. |
| 2016/0339233 | A1 | 11/2016 | De Kock et al. |
| 2017/0020551 | A1 | 1/2017 | Reddy et al. |
| 2017/0021159 | A1 | 1/2017 | Reddy et al. |
| 2017/0095657 | A1 | 4/2017 | Reddy et al. |
| 2017/0319845 | A1 | 11/2017 | De Kock et al. |
| 2017/0319864 | A1 | 11/2017 | De Kock et al. |
| 2018/0036527 | A1 | 2/2018 | Reddy et al. |
| 2018/0036547 | A1 | 2/2018 | Reddy |
| 2018/0078252 | A1 | 3/2018 | Sato |
| 2018/0133458 | A1 | 5/2018 | Foster et al. |
| 2018/0133462 | A1 | 5/2018 | Reddy |
| 2018/0133463 | A1 | 5/2018 | Reddy |
| 2018/0133494 | A1 | 5/2018 | Reddy |
| 2018/0169384 | A1 | 6/2018 | Reddy et al. |
| 2018/0169425 | A1 | 6/2018 | Reddy et al. |
| 2018/0193060 | A1 | 7/2018 | Reddy et al. |
| 2018/0214686 | A1 | 8/2018 | De Kock et al. |
| 2018/0296824 | A1 | 10/2018 | De Kock et al. |
| 2018/0344200 | A1 | 12/2018 | Thakur et al. |
| 2018/0344252 | A1 | 12/2018 | An et al. |
| 2019/0054289 | A1 | 2/2019 | Reddy et al. |
| 2019/0054290 | A1 | 2/2019 | De Kock et al. |
| 2019/0054302 | A1 | 3/2019 | Reddy et al. |
| 2019/0117959 | A1 | 4/2019 | Reddy |
| 2019/0151651 | A1 | 5/2019 | Reddy et al. |

OTHER PUBLICATIONS

International Search Report and Written Opinion dated Oct. 29, 2019 for International Application No. PCT/US2019/012995.
Invitation to Pay Additional Fees dated Jul. 26, 2019 for International Application No. PCT/US2019/028506.

* cited by examiner

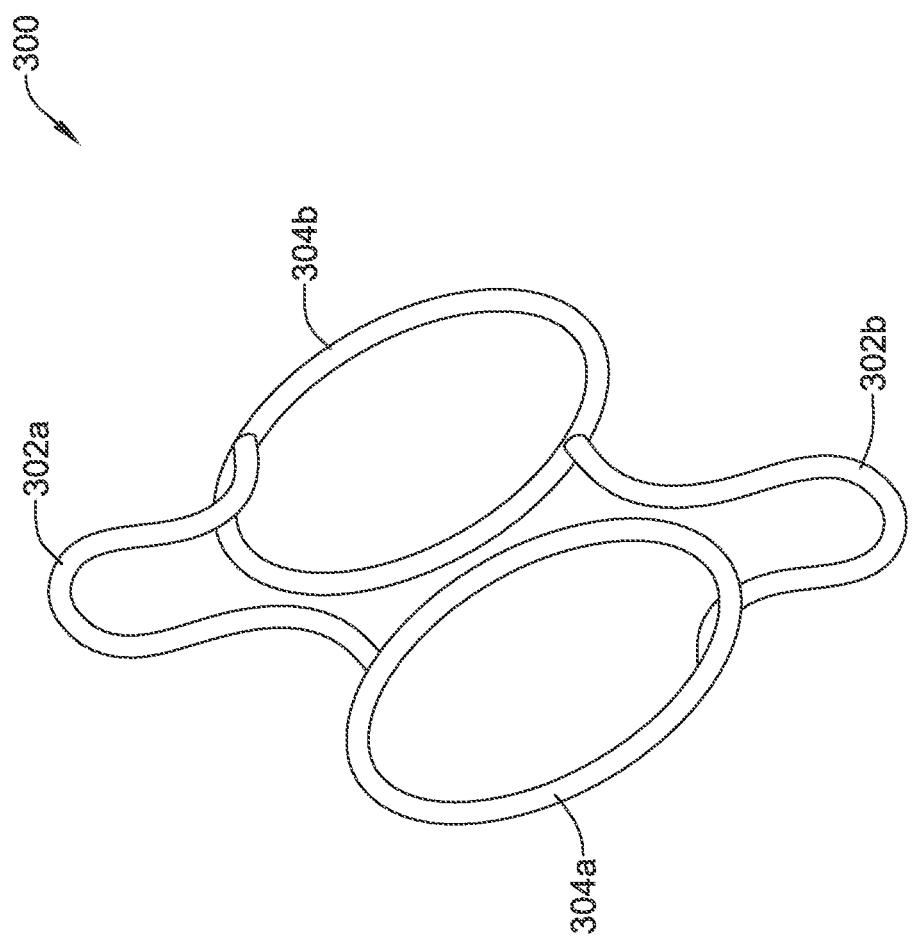

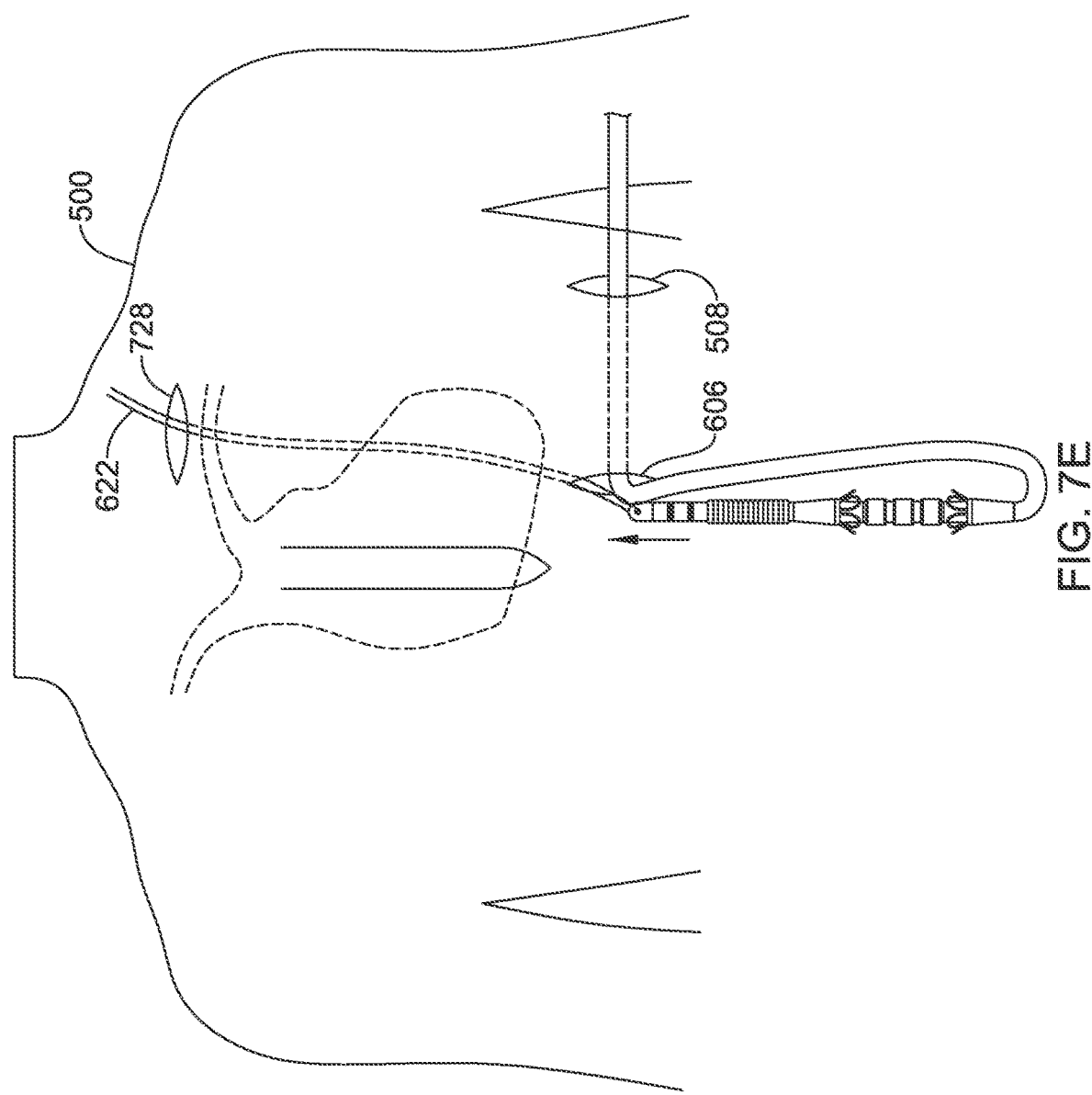

RETENTION MECHANISM FOR AN IMPLANTABLE LEAD

CROSS REFERENCE TO RELATED APPLICATIONS

The present application claims the benefit of and priority to U.S. Provisional Patent Application Ser. No. 62/665,216, filed May 1, 2018, titled RETENTION MECHANISM FOR AN IMPLANTABLE LEAD, the disclosure of which is incorporated herein by reference.

BACKGROUND

The subcutaneous implantable cardioverter-defibrillator (S-ICD System) from Boston Scientific is implanted, according to the original FDA labeling thereof, with a subcutaneous lead extending from an implanted pulse generator in an axillary pocket, over the ribs to the xiphoid process, and then superiorly along the left side of the sternum. The implant method as originally approved calls for a suture sleeve fixation near the xiphoid. To affix the suture sleeve at this location to the fascia requires the application of suture loops around the suture sleeve and attachment of the suture to the fascia, through a small 1-2 cm xiphoid incision.

The suturing steps that are used to secure the lead in position relative to the thorax are one element that extends procedure time. There is significant interest in reducing procedure time and simplifying the implant procedure by avoiding such suture steps. Moreover, the multiple incisions called for in the S-ICD System implantation procedure raise risks of infection and leave small but visible scars. This has led to interest in simplification of the implant procedure by reducing the number of incisions from 3 to 2, while continuing to ensure the lead is anchored in a desired position.

New and alternative methods and devices for securing a lead, whether for the S-ICD System or other devices, are desired.

Overview

The present inventors have recognized that a new and useful innovation may include a retention device and method of using a retention device for aiding in the placement of a lead. Such a retention device may be placed on a distal portion of a lead.

A first illustrative and non-limiting example is a retention device for use with an implantable medical device (IMD) that may include an elongate body having a proximal end, a distal end, a hollow lumen extending from the proximal end to the distal end configured to receive a lead of the IMD, and an outer surface having a first recess configured to receive a suture for tying purposes to secure the retention device at a desired location on the lead; and one or more securing mechanisms each having a first end and a second end each coupled to the elongate body and an intermediate section between the first end and the second end configured to push against tissue of a patient.

Additionally or alternatively to the first illustrative, non-limiting example, the one or more securing mechanisms each may define a loop. Additionally or alternatively to the first illustrative, non-limiting example, each of the one or more securing mechanisms may be capable of shifting between a delivery configuration and a deployed configuration. Additionally or alternatively to the first illustrative, non-limiting example, in the delivery configuration the one or more securing mechanisms may lay flat against the elongate body and the intermediate section may move in an axial direction and away from the elongate body to the deployed configuration.

Additionally or alternatively to the first illustrative, non-limiting example, in the delivery configuration the one or more securing mechanisms may be nested in a second recess of the elongate body. Additionally or alternatively to the first illustrative, non-limiting example, the one or more securing mechanisms may further include a first set of securing mechanisms and a second set of securing mechanisms, the second set of securing mechanisms may be spaced longitudinally away from the first set of securing mechanisms.

Additionally or alternatively to the first illustrative, non-limiting example, in a deployed configuration the first set of securing mechanisms may extend outward from the elongate body in a first direction at a first angle, and the second set of securing mechanisms may extend outward from the elongated body in a second direction at a second angle, wherein the first and second angles may be equal and the first and second directions may be opposite one another such that the sections of the first set of securing mechanisms may be closer to the sections of the second set of securing mechanisms than to the first end and the second end of the second set of securing mechanisms.

Additionally or alternatively to the first illustrative, non-limiting example, in the delivery configuration the one or more securing mechanisms may wrap around the elongate body. Additionally or alternatively to the first illustrative, non-limiting example, the one or more securing mechanisms may comprise a plurality of securing mechanisms circumferentially spaced from one another. Additionally or alternatively to the first illustrative, non-limiting example, the one or more securing mechanisms may be made of a flexible material. Additionally or alternatively to the first illustrative, non-limiting example, the flexible material may comprise nitinol wires. Additionally or alternatively to the first illustrative, non-limiting example, the flexible material may comprise a polymeric material. Additionally or alternatively to the first illustrative, non-limiting example, the flexible material may comprise silicone. Additionally or alternatively to the first illustrative, non-limiting example, at least one securing mechanism may be noose shaped.

Additionally or alternatively to the first illustrative non-limiting example, an implantable medical device system may include each of an implantable pulse generator comprising a canister housing operational circuitry adapted to generate a therapy output, a lead adapted for coupling to the implantable pulse generator and adapted to deliver the therapy output from the implantable pulse generator, and a retention device as in the first illustrative example and/or any of the above additions or alternatives thereto, wherein the lead is sized and shaped to be received in the hollow lumen of the retention device.

Additionally or alternatively to the first illustrative non-limiting example, a combination retention device and lead for use in an implantable medical device system may include a lead having an elongate shaft with a first end adapted to couple to an implantable pulse generator and a second end adapted for implantation in a patient and having one or more electrodes thereon, and a retention device as in the first illustrative example and/or any of the above additions or alternatives thereto, wherein the lead is sized and shaped to be received in the hollow lumen of the retention device.

A second illustrative, non-limiting example takes the form of a method of implanting an implantable lead in a patient comprising the use of an implantable lead having a first end for coupling to an implantable medical device and a second end for implantation at a target site in the patient, with a lead body extending therebetween and the retention device of the first illustrative, non-limiting example, wherein the method may comprise inserting the implantable lead into the patient with the retention device placed on the lead at a desired location thereon and with a sheath that may be disposed about at least a portion of the lead and compressing the one or more securing mechanisms of the retention device in a delivery configuration; and at least partly withdrawing the sheath such that the one or more securing mechanisms may move to a deployed configuration to anchor the implantable lead to tissue of the patient.

Additionally or alternatively to the second illustrative, non-limiting example, the step of inserting the implantable lead may be performed by making a single incision, advancing an insertion tool having the sheath thereon through the incision and to a selected position in the patient, removing the insertion tool while keeping the sheath in place, and then inserting the implantable lead into the sheath such that the sheath may compress the one or more securing mechanisms of the retention device into the delivery configuration.

Additionally or alternatively to the second illustrative, non-limiting example, the step of inserting the implantable lead may be performed by: making a first incision and a second incision; making a first tunnel between the first and second incisions; making a second tunnel from the second incision to an end location; and passing at least the second end of the implantable lead through the second incision to the end location.

Additionally or alternatively to the second illustrative, non-limiting example, the step of inserting the implantable lead may be performed such that the retention device may be accessible near the second incision, and the method may further comprise using a suture to anchor the retention device to the patient using the first recess to receive the suture at or near the second incision such that the one or more securing mechanisms and the suture may both be used to secure the lead in the selected position.

Additionally or alternatively to the second illustrative, non-limiting example, the step of inserting the implantable lead may be performed by: making a first incision, a second incision and a third incision; making a first tunnel between the first and second incisions; making a second tunnel between the second and third incisions; and passing at least the second end of the lead through the second incision to the third incision.

Additionally or alternatively to the second illustrative, non-limiting example, the step of inserting the implantable lead may be performed such that the retention device may be accessible near the second incision, and the method may further comprise using a suture to anchor the retention device to the patient using the recess to receive the suture at or near the second incision such that the one or more securing mechanisms and the suture may both be used to secure the lead in the selected position.

A third illustrative, non-limiting example takes the form of an implantable medical device (IMD) system that may comprise a housing; operational circuitry for at least one of analyzing biological signals and delivering therapy to a patient, the operational circuitry may be disposed in the housing; an implantable lead that may be configure to couple to the housing, the implantable lead may include: a lead body having a longitudinal axis extending between a proximal end and a distal end; one or more electrodes disposed on the lead body; one or more conductors coupled to the one or more electrodes; and a connector at the proximal end of the lead body for coupling the one or more conductors to the operational circuitry; and the retention device of the first illustrative, non-limiting example.

A fourth illustrative, non-limiting example takes the form of a method of implanting the IMD of the third illustrative, non-limiting example, that may comprise inserting the implantable lead and the housing into the patient with the retention device placed on the implantable lead at a desired location thereon and with a sheath compressing the one or more securing mechanisms of the retention device in a delivery configuration; and at least partly withdrawing the sheath such that the one or more securing mechanisms may move to a deployed configuration to anchor the implantable lead to tissue of the patient.

Additionally or alternatively to the fourth illustrative, non-limiting example, the step of inserting the implantable lead may performed by making a single incision, advancing an insertion tool having the sheath thereon through the incision and to a selected position in the patient, removing the insertion tool while keeping the sheath in place, and then inserting the implantable lead into the sheath such that the sheath may compress the one or more securing mechanisms of the retention device into the delivery configuration.

Additionally or alternatively to the fourth illustrative, non-limiting example, the step of inserting the implantable lead may be performed by: making a first incision and a second incision; making a first tunnel between the first and second incisions; making a second tunnel from the second incision to an end location; passing at least a portion of the implantable lead with the retention device thereon through the first tunnel with the sheath thereover or through the sheath; and passing at least the second end of the implantable lead through the second incision to the end location.

Additionally or alternatively to the fourth illustrative, non-limiting example, the step of inserting the implantable lead may be performed such that the retention device may be accessible near the second incision, and the method may further comprise using a suture to anchor the retention device to the patient using the first recess to receive the suture at or near the second incision such that the one or more securing mechanisms and the suture are may both be used to secure the lead in the selected position.

Additionally or alternatively to the fourth illustrative, non-limiting example, the step of inserting the implantable lead may be performed by: making a first incision, a second incision and a third incision; making a first tunnel between the first and second incisions; making a second tunnel between the second and third incisions; passing at least a portion of the implantable lead with the retention device thereon through the first tunnel with the sheath thereover, or through the sheath; and passing at least the second end of the lead through the second incision to the third incision.

Additionally or alternatively to the fourth illustrative, non-limiting example, the step of inserting the implantable lead may be performed such that the retention device may be accessible near the second incision, and the method may further comprise using a suture to anchor the retention device to the patient using the first recess to receive the suture at or near the second incision such that the one or more securing mechanisms and the suture may both be used to secure the lead in the selected position.

A fifth illustrative, non-limiting example takes the form of a retention device for use with an implantable medical device (IMD), the retention device may comprise an elongate body that may have a proximal end, a distal end, a hollow lumen extending from the proximal end to the distal end that may be configured to receive a lead of the IMD, and an outer surface that may have a first recess; and a first securing mechanism that may have first and second ends that may be configured to extend over and around at least a portion of the elongate body and an intermediate section between the first end and the second end that may be configured to push against tissue of the patient, wherein the first recess may be adapted to receive at least one end of the first securing mechanism.

Additionally or alternatively to the fifth illustrative, non-limiting example, the first end of the first securing mechanism may be further configured to slide toward the second end, moving the intermediate section in a radial direction away from the elongate body, so as to define a deployed configuration in which each of the first and second ends of the first securing mechanism may reside in the first recess of the elongate body, and a delivery configuration in which only one of the first and second ends of the first securing mechanism may reside in the first recess.

Additionally or alternatively to the fifth illustrative, non-limiting example, when the intermediate section moves in the radial direction away from the elongate body, the intermediate section may include a curve. Additionally or alternatively to the fifth illustrative, non-limiting example, the first securing mechanism when in the delivery configuration, may lie flat against the elongate body, and, when in the deployed configuration, the intermediate section may extend radially out from the elongate body to serve as an anchor in tissue. Additionally or alternatively to the fifth illustrative, non-limiting example, the first and second ends of the first securing mechanism may comprise wires that encircle the elongate body and the intermediate section may include two or more wires having first ends connected to the first end of the securing mechanism and second ends connected to the second end of the securing mechanism. Additionally or alternatively to the fifth illustrative, non-limiting example, the wires may be nitinol wires.

Additionally or alternatively to the fifth illustrative, non-limiting example, the elongate body may comprise one or more tines, hooks, tabs, or loops extending therefrom to serve as anchoring mechanisms.

Additionally or alternatively to the fifth illustrative, non-limiting example, further comprising a second securing mechanism having first and second ends in the form of loops that may encircle the elongate body and an intermediate section that may have at least first and second wires extending between the first and second ends, wherein the elongate body may comprise a second recess, further wherein the first end of the second securing mechanism may be further configured to slide toward the second end of the second securing mechanism, moving the intermediate section in a radial direction away from the elongate body so as to define a deployed configuration in which each of the first and second ends of the second securing mechanism may reside in the second recess of the elongate body, and a delivery configuration in which only one of the first and second ends of the second securing mechanism may reside in the second recess.

A sixth illustrative, non-limiting example takes the form of a method of implanting an implantable lead in a patient comprising the use of an implantable lead that may have a first end for coupling to an implantable medical device and a second end for implantation at a target site in the patient, with a lead body extending therebetween and the retention device of the fifth illustrative, non-limiting example, the method may comprise inserting the implantable lead into the patient with the retention device placed on the lead at a desired location thereon; and sliding the first end of the first securing mechanism toward the second end of the first securing mechanism causing the intermediate section of the first securing mechanisms to move radially away from the elongate body to a deployed configuration to anchor the implantable lead to tissue of the patient.

Additionally or alternatively to the sixth illustrative, non-limiting example, the step of inserting the implantable lead may be performed by making a single incision, advancing an insertion tool having a sheath thereon through the incision and to a selected position in the patient, removing the insertion tool while keeping the sheath in place, and then inserting the implantable lead into the sheath with the retention device on the lead.

Additionally or alternatively to the sixth illustrative, non-limiting example, the step of inserting the implantable lead may be performed by: making a first incision and a second incision; making a first tunnel between the first and second incisions; making a second tunnel from the second incision to an end location; and passing at least the second end of the implantable lead through the second incision to the end location.

Additionally or alternatively to the sixth illustrative, non-limiting example, the step of inserting the implantable lead may be performed such that the retention device may be accessible near the second incision, and the method may further comprise using a suture to anchor the retention device to the patient at or near the second incision such that the first securing mechanism and the suture may both be used to secure the lead in the selected position.

Additionally or alternatively to the sixth illustrative, non-limiting example, the step of inserting the implantable lead may be performed by: making a first incision, a second incision and a third incision; making a first tunnel between the first and second incisions; making a second tunnel between the second and third incisions; and passing at least the second end of the lead through the second incision to the third incision.

Additionally or alternatively to the sixth illustrative, non-limiting example, the step of inserting the implantable lead may be performed such that the retention device may be accessible near the second incision, and the method may further comprise using a suture to anchor the retention device to the patient at or near the second incision such that the first securing mechanism and the suture may both be used to secure the lead in the selected position.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3A-3E show an example securing mechanism;

FIGS. 7A-7F illustrate a third method for implanting the implantable medical device.

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives. In the methods shown below, structures may be beneath the skin and over the ribcage of the patient, though such elements are not always shown in phantom. Some examples may place devices in the abdomen, again making use of suturing techniques that anchor to the fascia.

The words "proximal" and "distal" are used herein to differentiate the ends of devices. No specific anatomical significance is intended. For example, the distal end of a lead is not necessarily anatomically distal relative to the proximal end of the lead; anatomic distal and proximal terminology will be determined by the final implantation location(s).

Figure 1A:
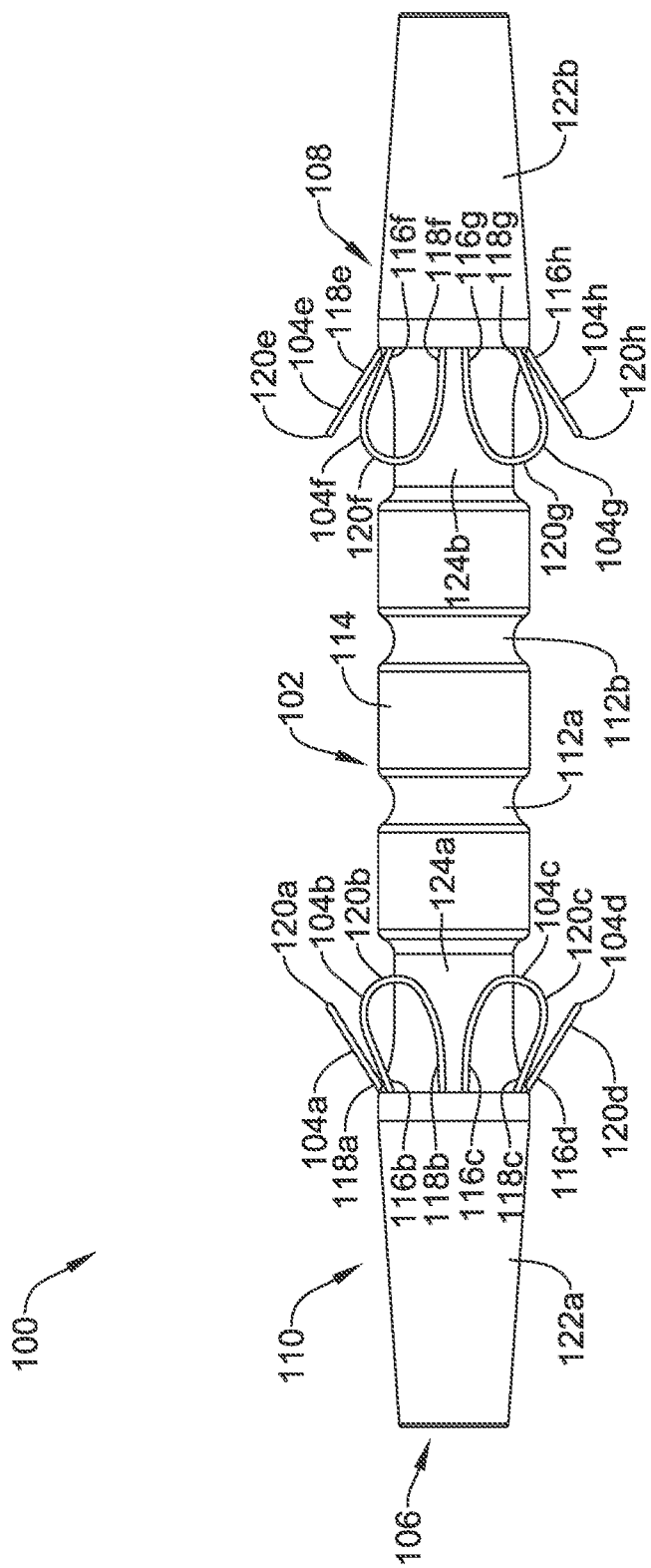
FIGS. 1A-1B show a first example retention device.
Figure 1B:
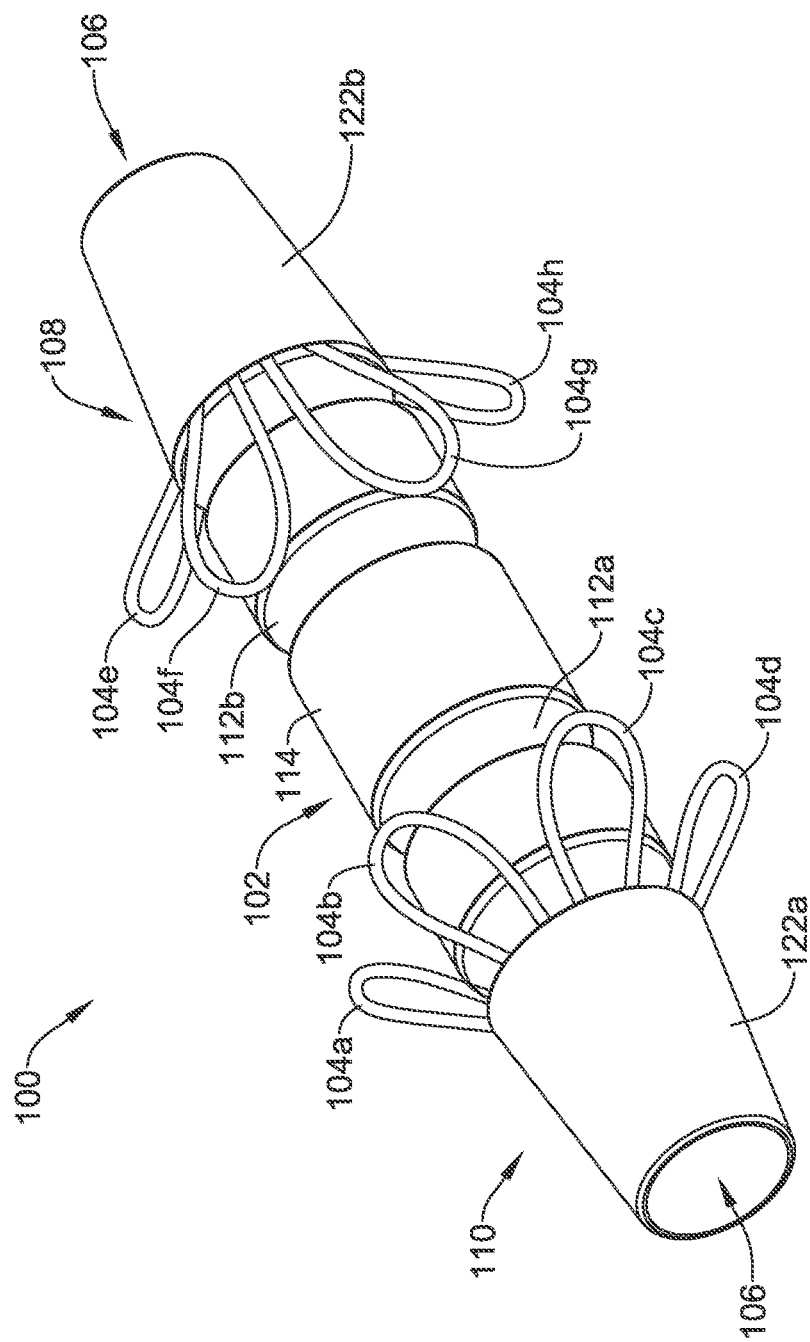

FIG. 1A depicts an illustrative side-view of an example retention device 100 and FIG. 1B depicts an illustrative isometric-view of the example retention device 100. As shown, the retention device 100 may include an elongate body 102 and two sets of securing mechanisms, a first set 104A-104D and a second set 104E-104H spaced longitudinally, along the elongate body 102, away from the first set 104A-104D. While two sets of securing mechanisms are shown in this illustrative example, other examples may have only one set of securing mechanisms, while other examples may have three or more sets of securing mechanisms distributed along the length of a retention device. According to various embodiments, the elongate body 102 may have a hollow lumen 106 that extends from an open distal end 108 to an open proximal end 110. In an example, the hollow lumen 106 is dimensioned to receive a portion of an implantable lead therein. The elongate body 102 may be formed from any material suitable for chronic implantation in patients, such as a wide variety of plastics and/or metals. Different parts may be made of different materials, or may have additional structure, such as by using coated wires for the securing mechanisms and an extruded tube for the elongate body, or the entire piece may be formed in a single molding step of a single material.

The elongate body 102 may also include one or more recesses 112A-112B on an outer surface 114 that can receive a suture to assist in securing the retention device 100 at a desired location on the lead. The inclusion of several such recesses 112A-112B may allow more structural flexibility or greater force to be applied to hold the retention device 100 on a lead. For example, tightening the suture onto the elongate body 102 while in a recess 112A and/or 112B can reduce the diameter of the hollow lumen 106 to secure the retention device 100 onto a lead.

In some examples, a suture may also be used to secure the retention device 100 at a selected position in the patient. In some examples, the inclusion of several recesses 112A-112B offers a wider range of options for positional alignment of an implanted lead or electrode to patient anatomy. Two recesses 112A, 112B are shown; other examples may use 1, 3, or more recesses, or the recesses 112A, 112B may be omitted entirely. In other examples, particularly those that are adapted to place the device 100 without suturing it to the patient's tissue, the securing mechanisms 104A-104H are solely relied upon to anchor the retention device 100.

In some cases, the securing mechanisms 104A-104H may be configured to push against tissue of the patient when the retention device 100 is implanted inside the patient. In some cases, the first set of securing mechanisms 104A-104D may be circumferentially spaced from one another around the elongate body 102 at the proximal end 110 and the second set of securing mechanisms 104E-104H may also be circumferentially spaced from one another around the elongate body 102 at the distal end 108. In some examples, the securing mechanisms 104A-104H may be fixation loops that are a formed, single-piece, with the elongate body 102. In some cases, the securing mechanisms 104A-104H may have first ends 116A-116H and second ends 118A-118H attached to the elongate body 102 in any suitable manner, which may include hinges, screws, pins and/or any other suitable fastener. In on example, a wire frame may be formed first to establish the structure of the device 100, including loops for the securing mechanisms 104A-104H and a coil or mesh tube for elongate body 102, on which a polymeric coating can be applied by spraying, dipping or insert molding.

In some cases, the first ends 116A-116H and the second ends 118A-118H of the securing mechanisms 104A-104H may be molded to the elongate body 102 so that joints are formed. In some cases, the joints may be configured to pivot so that intermediate sections 120A-120H of the securing mechanisms 104A-104H move, shift, retract, or compress towards the elongate body 102, in an axial and/or radial direction, to a delivery configuration. For instance, the joints may be configured to pivot so that the intermediate sections 120A-120H move, shift, swing, or extend away from the elongate body 102, in both an axial and radial direction, to a deployed configuration. In some cases, rather than a defined joint, the securing mechanisms may simply flex, move, and/or shift toward and away from the elongate body 102.

As shown in FIGS. 1A and 1B, the outer surface 114 of the retention device 100 may have a diameter that varies along the elongate body 102. In some examples, the outer surface 114 may include tapered sections 122A and 122B that taper, incline, or slope, to a smaller diameter from a larger diameter at the location where the first ends 116A-116H and the second ends 118A-118H of the securing mechanisms 104A-104H attach to the retention device 100. In some cases, the outer surface 114 may include recesses 124A and 124B to allow the securing mechanisms 104A-104H to be folded down to a delivery configuration and nested in the recesses 124A and 124B, for introduction into a patient. That is, the recesses 124A and 124B may be designed, such that when the securing mechanisms 104A-104H are folded down, they do not increase the outer diameter of the retention device 100. As such, when the securing mechanisms 104A-104H are in the delivery configuration, the intermediate sections 120A-120H of the securing mechanisms may be located adjacent to the smaller diameter portion of the recesses 124A and 124B. When disposed in a sheath, the outer diameter of the sheath may be generally smooth as a result, avoiding trauma to the patient during insertion.

In some cases, the securing mechanisms 104A-104H may be comprised of the same materials as the elongate body 102. However, in some embodiments, the securing mechanisms 104A-104H may be comprised of different materials than the elongate body 102. In some examples, the securing mechanisms 104A-104H may be comprised of a different, stiffer, material than the elongate body 102. Alternatively, the securing mechanisms 104A-104H may be softer than the elongate body 102. In some examples, the securing mechanisms may be formed of silicone while a different polymer of stiffer or harder character is used for the elongate body 102. In other examples, the securing mechanisms may be coated or uncoated nitinol wires or other metal wires, making them generally stiffer than the elongate body. In some cases, the securing mechanisms 104A-104H may be radiopaque. Alternatively or additionally, the elongate body or portions thereof may be radiopaque.

In some cases, the securing mechanisms 104A-104H may be circumferentially spaced from one another to enable the retention device 100 to be collapsed by a sheath to a delivery configuration. When the retention device 100 is in a selected position or configuration during implantation in the patient, the sheath may be removed. Upon removal of the sheath, the securing mechanisms 104A-104H may expand to engage, push against, and/or anchor the retention device 100 in a desired location such as the subcutaneous tissue of a patient.

In one example, a shape memory material is used for the securing mechanisms 104A-104H, such that a delivery configuration may be achieved with little tension exerted by the securing mechanisms until body temperature is reached during implantation. Once implanted and with the insertion sheath removed, the shape memory material can then cause the securing mechanisms to spring outward, anchoring to the surrounding tissue.

In some instances, the securing mechanisms 104A-104H may each be comprised of a nitinol wire and the first ends 116A-116H and the second ends 118A-118H may be attached to elongate body 102. In some cases, the intermediate sections 120A-120H, may extend out from the first ends 116A-116H and come back around to the second ends 118A-118H, such that each of the securing mechanism 104A-104H Mine a loop. In some cases, the loop may have a noose shape configuration. In some cases, the loop may be tine shaped, hook shaped, fan shaped, rectangular shaped, a combination thereof, etc. A loop shape may be useful in a subcutaneous implant configuration partly because it is less likely to pierce through tissue layers, in particular, the skin, while still being able to secure within the loose connective tissue and subcutaneous fat layer between the skin and the fascia.

In some cases, as depicted in FIGS. 1A and 1B and as stated above, there may be several securing mechanisms 104A-104H that are circumferentially spaced from one another around the elongate body 102. In some cases, the securing mechanisms 104A-104H may be limited to one side of the elongate body 102. In some instances, there may be a single securing mechanism 104A.

In some examples, the loop shapes of the securing mechanisms 104A-104H may vary from one another. For example, different securing mechanisms 104A-104A may have different lengths or widths of intermediate sections 120A-120H. In some examples such as that shown, the intermediate sections 120A-120H may all have the same width, length and shape.

In some examples, the securing mechanisms 104A-104H may be attached to the elongate body 102 such that the securing mechanisms 104A-104H have a desired degree of angular separation with the elongate body 102 in the deployed configuration. For example, the securing mechanisms 104A-104H may be configured so that there is a 45° angle of separation between the securing mechanisms 104A-104H and the elongate body 102. In some cases, the angle of separation may be 15°, 30°, 60°, 90°, etc. In some cases, the angles of separation may be substantially the same or equal across each of the securing mechanisms 104A-104H. In some cases, the angles of separation may not be the same or equal to one another. Thus, while the examples shown generally have sets of securing mechanisms 104A-104H that are symmetrically placed about the circumference of the retention device 100 with similar angular and shape characteristics, this need not be the case and different ones of the securing mechanisms 104A-104H may be differently oriented, sized or shaped, if desired.

In addition, different ones of the securing mechanisms 104A-104H may have differing material properties, if desired. The various noted variations in shape, quantity, distribution, size, orientation, angular configuration, etc. may be incorporated in any of the following illustrative examples. In some examples such as the one shown, in the deployed configuration, the first set of securing mechanisms 104A-104D may extend radially outward from the elongate body 102 at a first angle and the second set of securing mechanisms 104E-104H may extend radially outward from the elongate body 102 at a second angle, equal to and opposite the first angle. In this configuration, the intermediate sections 120A-120D of the first set of securing mechanisms 104A-104D may be closer to the intermediate sections 120E-120H of the second set of securing mechanisms 104E-104H than the first ends 116E-116H and second ends 118E-118H of the second set of securing mechanisms 104E-104H.

Figure 1C:
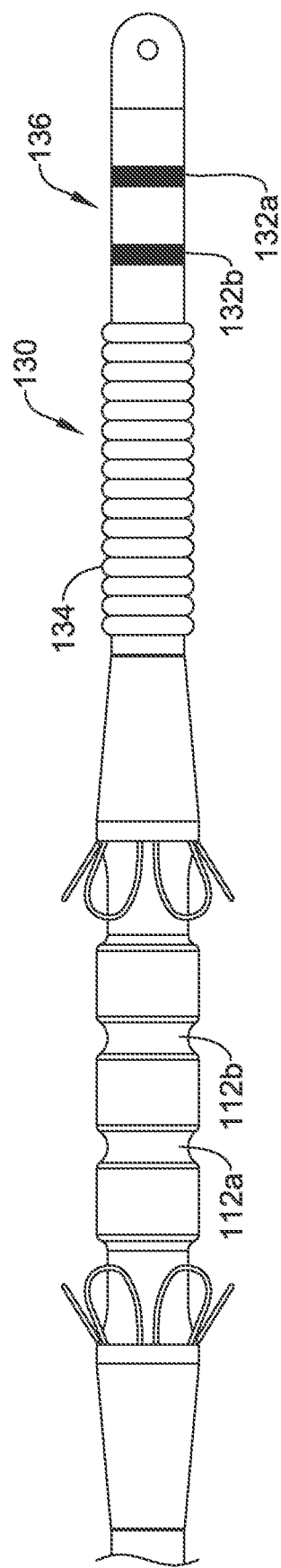
FIG. 1C shows the first example retention device coupled to a lead.

FIG. 1C depicts the example retention device 100 coupled to an illustrative implantable lead 130. In some cases, as shown in FIG. 1C, the retention device may be coupled to the implantable lead 130 by placing the implantable lead 130 through the hollow lumen 106 of the retention device 100 such that the retention device 100 substantially surrounds the lead 130. In some examples, the lead 130 may include ring electrodes illustrated at 132A, 132B as well as coil electrodes 134, though other electrode types and quantities may be used. For example, a directional electrode array may be used. The lead 130 may be manufactured of any suitable material and by any suitable manner. As noted above, a suture may be applied to the retention device 100 at the recesses 112A and/or 112B thereof to secure the retention device 100 to the lead 130 prior to or during implantation.

Figure 2A:
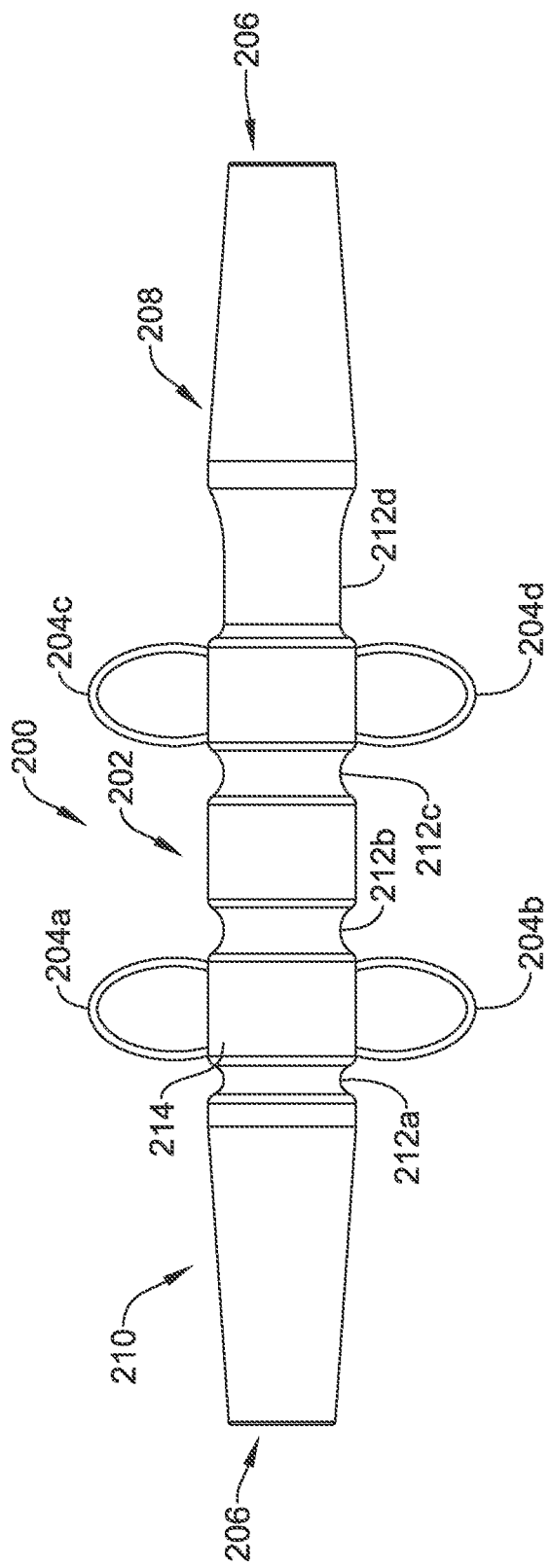
FIGS. 2A-2B show a second example retention device.
Figure 2B:
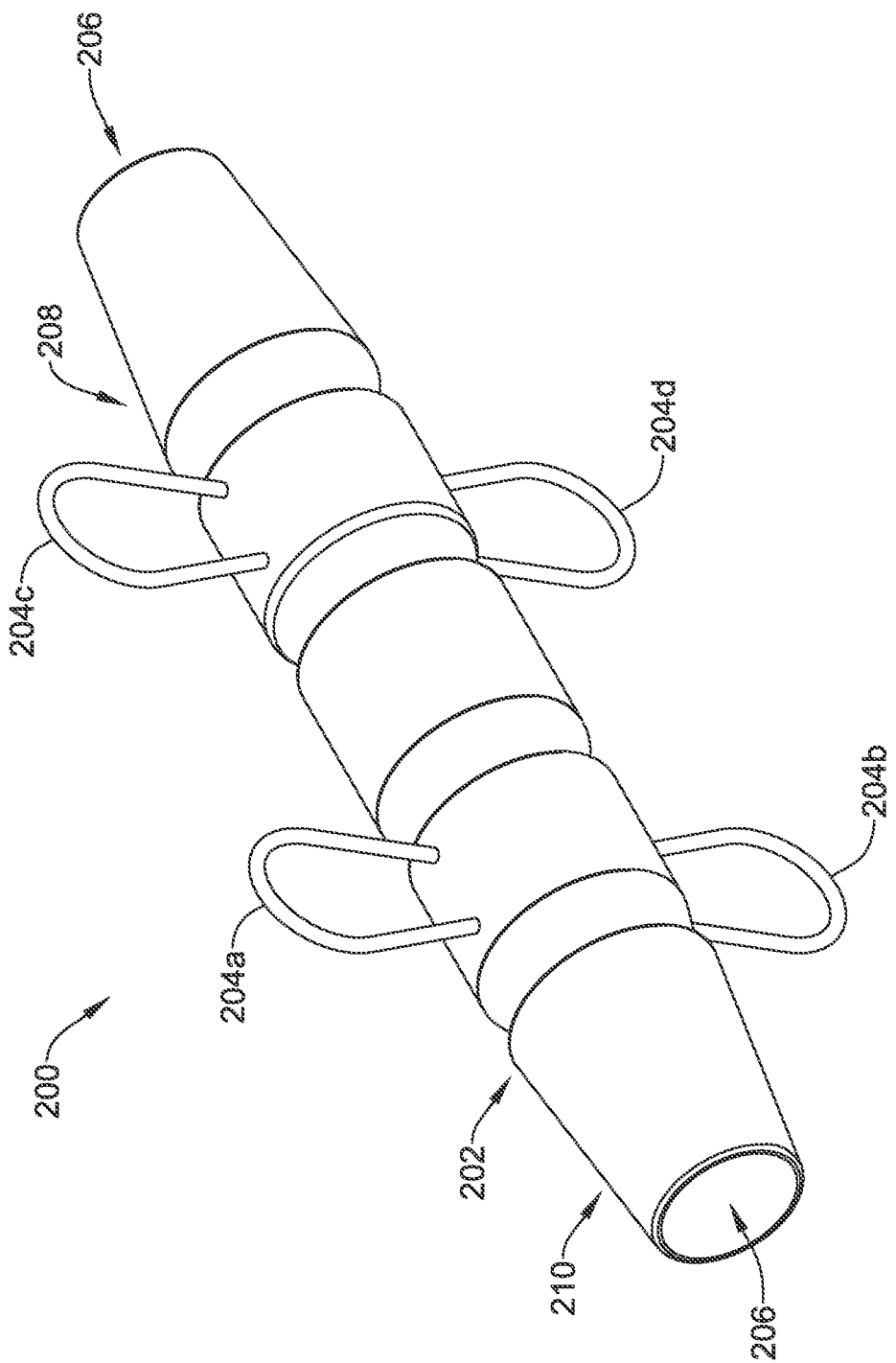

FIG. 2A depicts an illustrative side-view of a second example retention device 200 and FIG. 2B depicts an illustrative isometric-view of the example retention device 200. As shown, the retention device 200 may include an elongate body 202 and two sets of securing mechanisms, a first set 204A and 204B and a second set 204C and 204D spaced longitudinally, along the elongate body 202, away from the first set 204A, 204B. Similar to the retention device 100, the elongate body 202 may have a hollow lumen 206 that extends from an open distal end 208 to an open proximal end 210 and can receive a portion of an implantable lead therein. The elongate body 202 may also include recesses 212A-212D that can each receive sutures for securing the retention device 200 to an implantable lead and/or secure the retention device 200 at a selected position in a patient. Similar to the retention device 100, retention device 200 may have a diameter that varies along the elongate body 202. The elongate body 202 may also be made of any suitable material for chronic implantation in patients, similar to the elongate body 102 of the retention device 100.

In some cases, the first set of securing mechanisms 204A and 204B may be circumferentially spaced from one another around the elongate body 202 at the proximal end 210 and the second set of securing mechanisms 204C and 204D may also be circumferentially spaced from one another around the elongate body 202 at the distal end 208. As shown in this example, the securing mechanisms 204A-204D may be fixation loops that are formed and/or comprised of similar materials as securing mechanisms 104A-104H and operate similar to securing mechanisms 104A-104H. However, in this example, the securing mechanism 204A-204D may flex, move, and/or shift such that the securing mechanisms 204A-204D wrap around the circumference of the elongate body 202, into a delivery configuration. In the delivery configuration, the securing mechanisms 204A-204D may lie flat against an outer surface 214 of the elongate body 202. When disposed in a sheath, the outer diameter of the sheath may be generally smooth as a result, avoiding unnecessary trauma to the patient during insertion. In some cases, the securing mechanisms 204A-204D may move, shift, expand, or flex away from the elongate body 202, in a circumferential and/or radial direction, to a deployed configuration. In some cases, in the deployed configuration, the securing mechanism 204A-204D may push against the tissue of a patient when the retention device 200 is implanted inside the patient. Similar to securing mechanisms 104A-104H, variations in shape, quantity, distribution, size, orientation, angular configuration, separation, etc. of the securing mechanisms 204A-204D may be incorporated in any of the following illustrative examples.

Figure 2C:
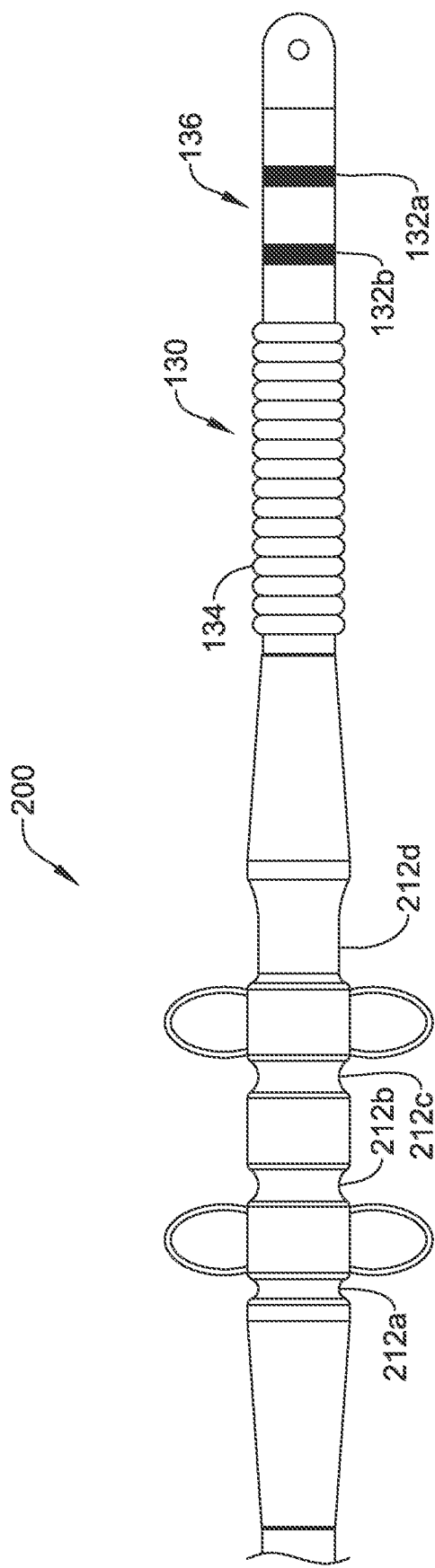
FIG. 2C shows the second example retention device coupled to the lead.

FIG. 2C depicts the example retention device 200 coupled to the illustrative implantable lead 130, In some cases, as shown in FIG. 1C, the retention device 200 may be coupled to the implantable lead 130 by placing the implantable lead 130 through the hollow lumen 206 of the retention device 200 such that the retention device 200 substantially surrounds the lead 230. As noted above, a suture may be applied to the retention device 200 at any or all the recesses 212A-212D thereof to secure the retention device 200 to the lead 130 prior to or during implantation.

Figure 3A:
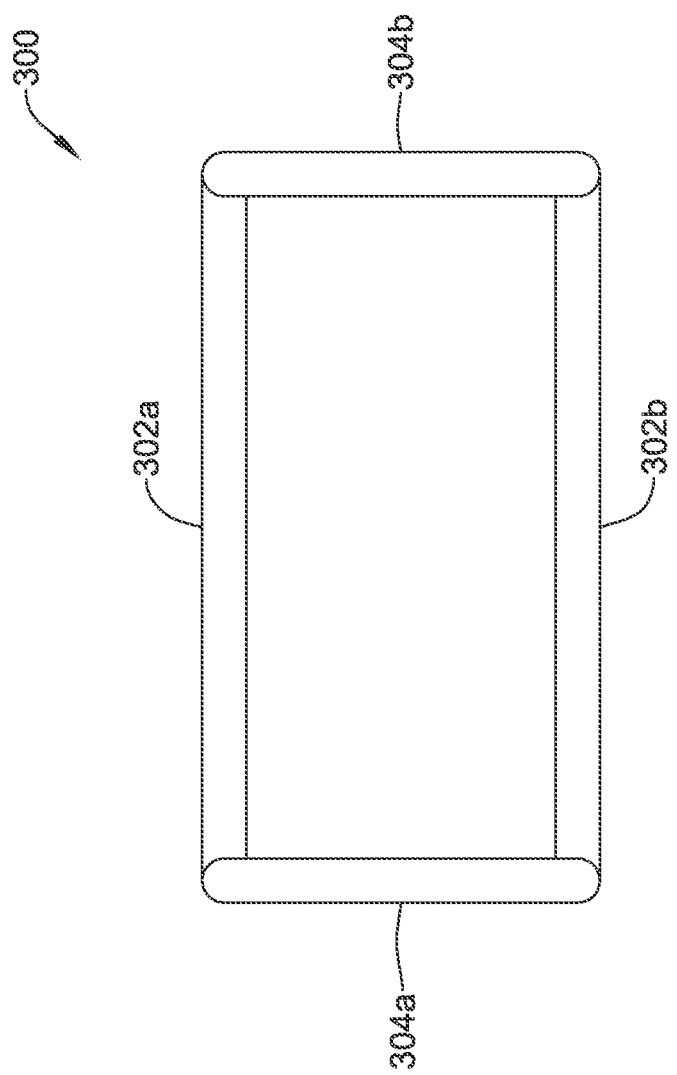
Figure 3B:
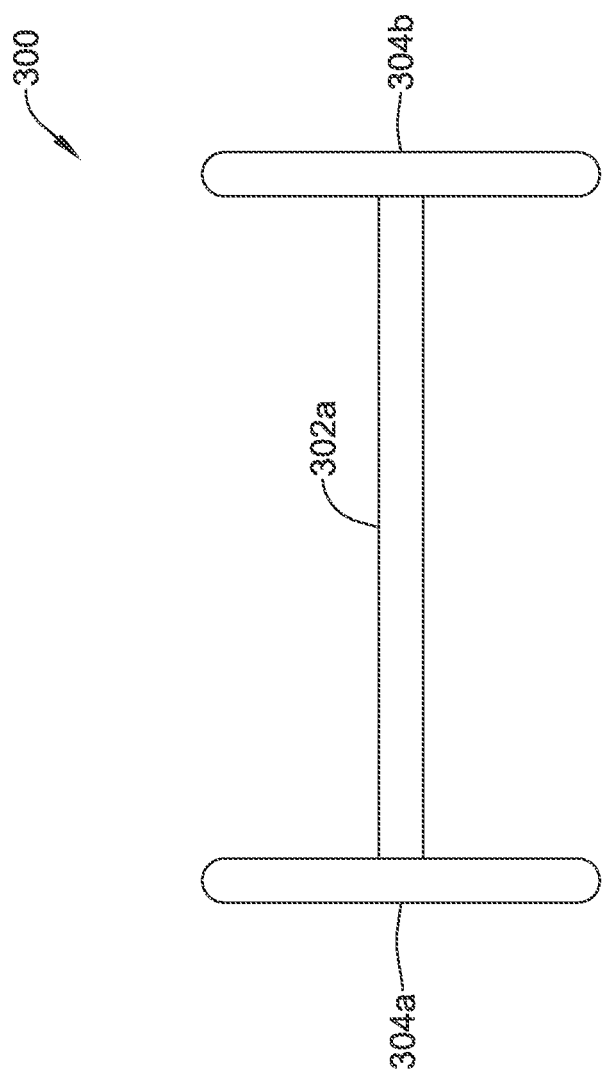
Figure 3C:
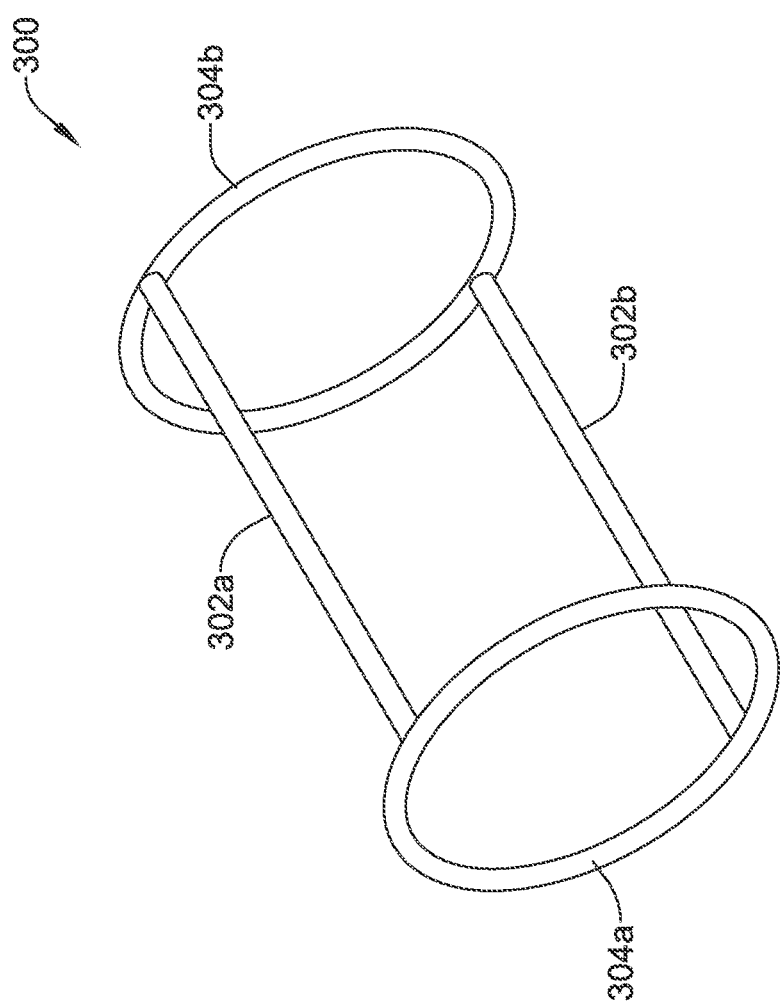

FIG. 3A depicts an illustrative side-view of another example securing mechanism 300 in a delivery configuration, FIG. 3B depicts an illustrative top-view of the securing mechanism 300 in the delivery configuration, and FIG. 3C isometric-view of the example securing mechanism 300 in the delivery configuration. The securing mechanism 300 may be comprised of similar materials as securing mechanisms 104A-104H and securing mechanism 204A-204D. In some cases, the securing mechanism 300 may include first and second ends 304A and 304B and an intermediate section that includes fixation loops 302A and 302B. In some cases, the first and second ends 304A and 304B may be configured to extend over and around an elongate body of second device, as shown below. In some cases, the first and second ends 304A and 304B may comprise wires, for example nitinol wires that encircle an elongate body and the intermediate section may include multiple fixation loops that are attached at one end to the first end 304A and another end attached to the second end 304B of the securing mechanism.

Figure 3D:
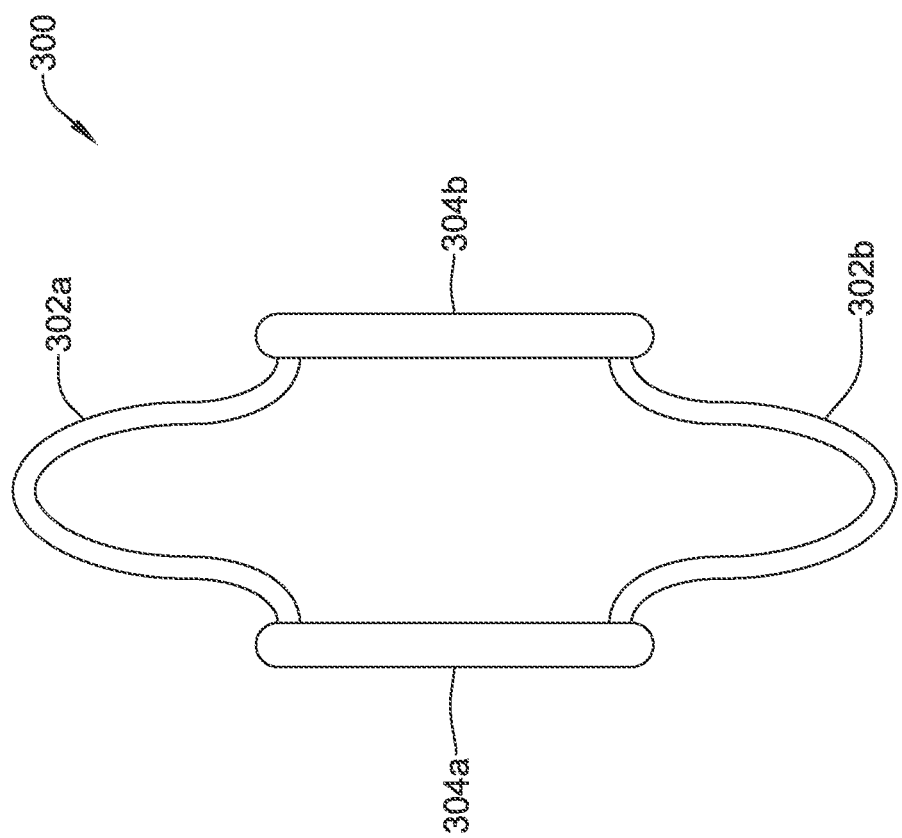

Furthermore, when the first and second ends 304A and 304B are moved towards one another, the fixation loops 302A and 302B may curve, crimp, fold, and/or compress to form loops. As such, when the first and second ends 304A and 304B are moved towards one another, the securing mechanism 300 may move from the delivery configuration to a deployed configuration. For instance, FIG. 3D depicts an illustrative side-view of the example securing mechanism 300 in the deployed configuration and FIG. 3E depicts an illustrative isometric-view of the example securing mechanism 300 in the deployed configuration. As highlighted in FIGS. 3C and 3E, the first and second ends 304A, 304B may be characterized as including encircling portions that will (as shown in FIGS. 4A-4B) encircle an elongate body once in a desired position.

Figure 4A:
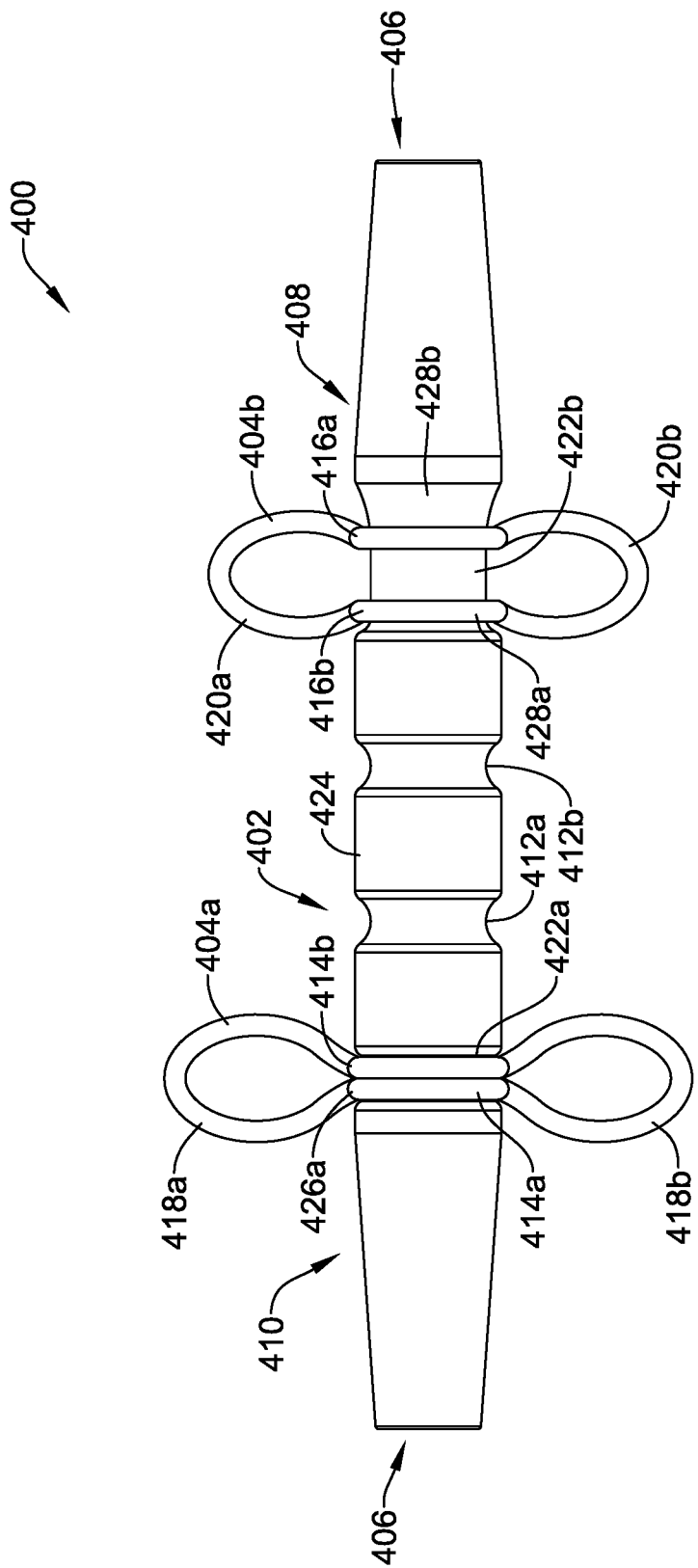
FIG. 4A shows example securing mechanisms coupled to an example elongate body.
Figure 4B:
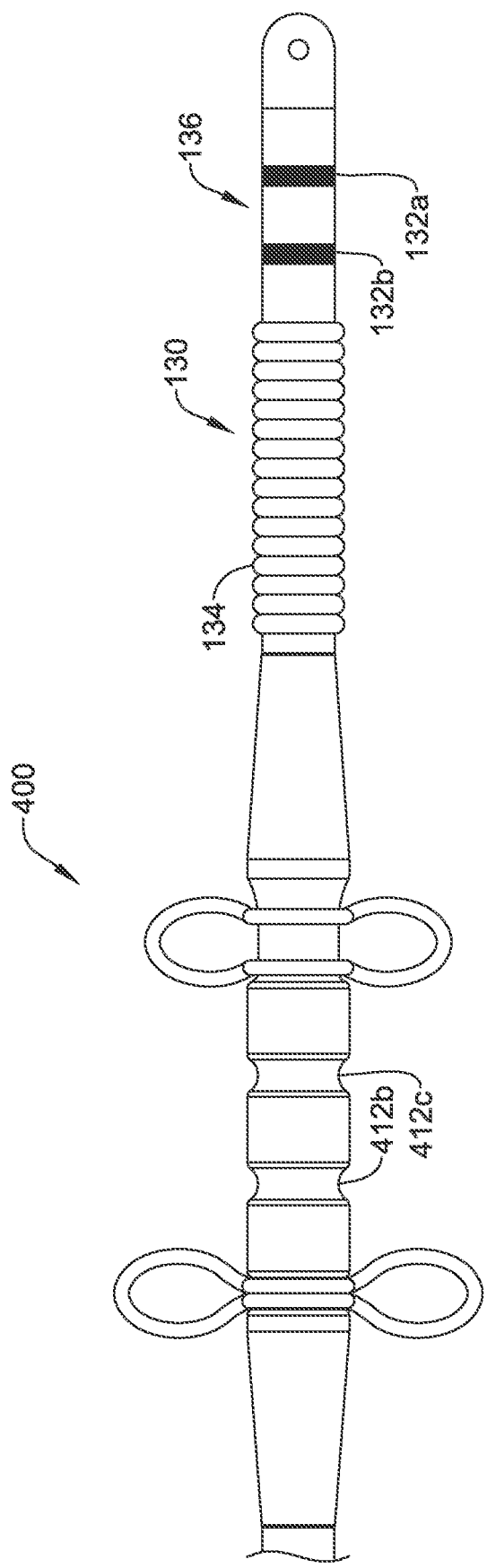
FIG. 4B shows the elongate body with the example securing mechanisms coupled to the lead.

FIG. 4A depicts an illustrative side-view of an example retention device 400. In some cases, the retention device 400 may include an elongate body 402 and securing mechanisms 404A and 404B. In this example, the elongate body 402 and securing mechanisms 404A and 404B are three separate pieces, with the elongate body 402 sized and adapted to receive the securing mechanisms 404A and 404B thereon.

The elongate body 402 may have a hollow lumen 406 that extends from an open distal end 408 to an open proximal end 410 and can receive a portion of an implantable lead therein. The elongate body 402 may also include recesses 412A and 412B that can each receive sutures for securing the retention device 400 to an implantable lead and/or secure the retention device 400 at a selected position in a patient. Retention device 400 may have a diameter that varies along the elongate body 402, including tapered or sloped regions shown at 408 and 410. The elongate body 402 may also be made of any suitable material for chronic implantation in patients, including various metals, plastics and combinations thereof.

Figure 4C:
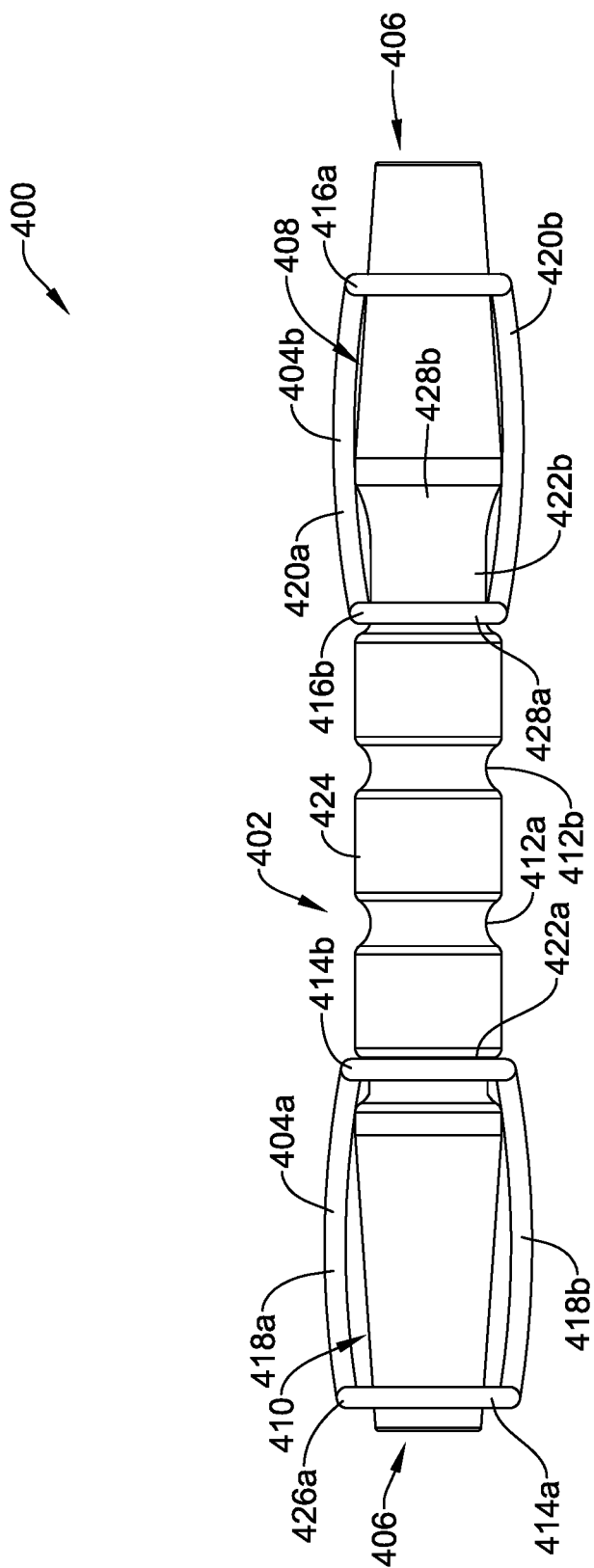
FIG. 4C shows the example securing mechanisms coupled to an elongate body in a delivery configuration.

The securing mechanisms 404A and 404B may be configured similar to and operate similar to securing mechanism 300 shown above in FIGS. 3A-3E. For example, securing mechanism 404A may include first and second ends 414A and 414B and an intermediate section between the first and second ends 414A and 414B that includes fixation loops 418A and 418B. Similarly, securing mechanism 404B may include first and second ends 416A and 416B and an intermediate section between the first and second ends 416A and 416B that includes fixation loops 420A and 420B. In some cases, the first and second ends 414A, 414B and 416A, 416B may be configured to extend over the tapered distal and proximal ends 408, 410 and around the elongate body 402. In some cases, in a delivery configuration in a delivery configuration as shown in FIG. 4C, the first ends 414A, 416A may substantial surround the distal and proximal ends 408, 410 and the second ends 414B, 416B may nest or reside in recesses 422A and 422B. In this way, again as shown in FIG. 4C, for the delivery configuration, the securing mechanisms 404A and 404B may lie relatively flat against an outer surface 424 of the elongate body 402. When disposed in a sheath, the outer diameter of the sheath may be generally smooth as a result, avoiding trauma to the patient during insertion.

When the retention device 400 is placed inside a patient and a sheath used for implantation is withdrawn, the first ends 414A, 416A may be moved, slid, and/or shifted along the elongate body 402 towards the second ends 414B, 416B into recesses 422A and 422B, as shown by the arrows in FIG. 4A. As the first ends 414A, 416A are drawn near to one another, the intermediate sections of securing mechanisms 404A and 404B (i.e., the fixation loops 418A, 418B and 420A, 420B) move radially away from the elongate body 402 into a deployed configuration. To facilitate the sliding motion, the encircling portions of the first and second ends of the securing mechanisms 404A, 404B may each have elastic characteristics to allow expansion as each passes over the tapered sections of the elongate body 408, 410 and recovery to assume and hold the deployed configuration.

In some cases, in the deployed configuration, the fixation loops 418A, 418B and 420A, 420B may define loops or noose shapes. Furthermore, since both ends of the securing mechanisms 404A and 404B reside in the recesses 422A and 422B, the securing mechanisms 404A and 404B may be held in the deployed configuration by ledges 426A, 426B and 428A, 428B of the recesses 422A and 422B. In some cases, in the deployed configuration, the securing mechanism 404A and 404B may push against the tissue of a patient when the retention device 400 is implanted inside the patient. Similar to securing mechanisms 104A-104H and 204A-204D, variations in shape, quantity, distribution, size, orientation, angular configuration, separation, etc. of the securing mechanisms 404A and 404B may be incorporated in any of the following illustrative examples.

FIG. 4B depicts the example retention device 400 coupled to the illustrative implantable lead 130. In some cases, as shown in FIG. 4B, the retention device 400 may be coupled to the implantable lead 130 by placing the implantable lead 130 through the hollow lumen 406 of the retention device 400 such that the retention device 400 substantially surrounds the lead 130. As noted above, a suture may be applied to the retention device 400 at any or all the recesses 412A and 412B thereof to secure the retention device 400 to the lead 130 prior to or during implantation. In some examples, the encircling portions of the first ends 414A, 416A of the securing mechanisms 404A, 404B are sized such that, once placed on the elongate body 402, the elongate body 402 becomes crimped down onto the lead.

Figure 5A:
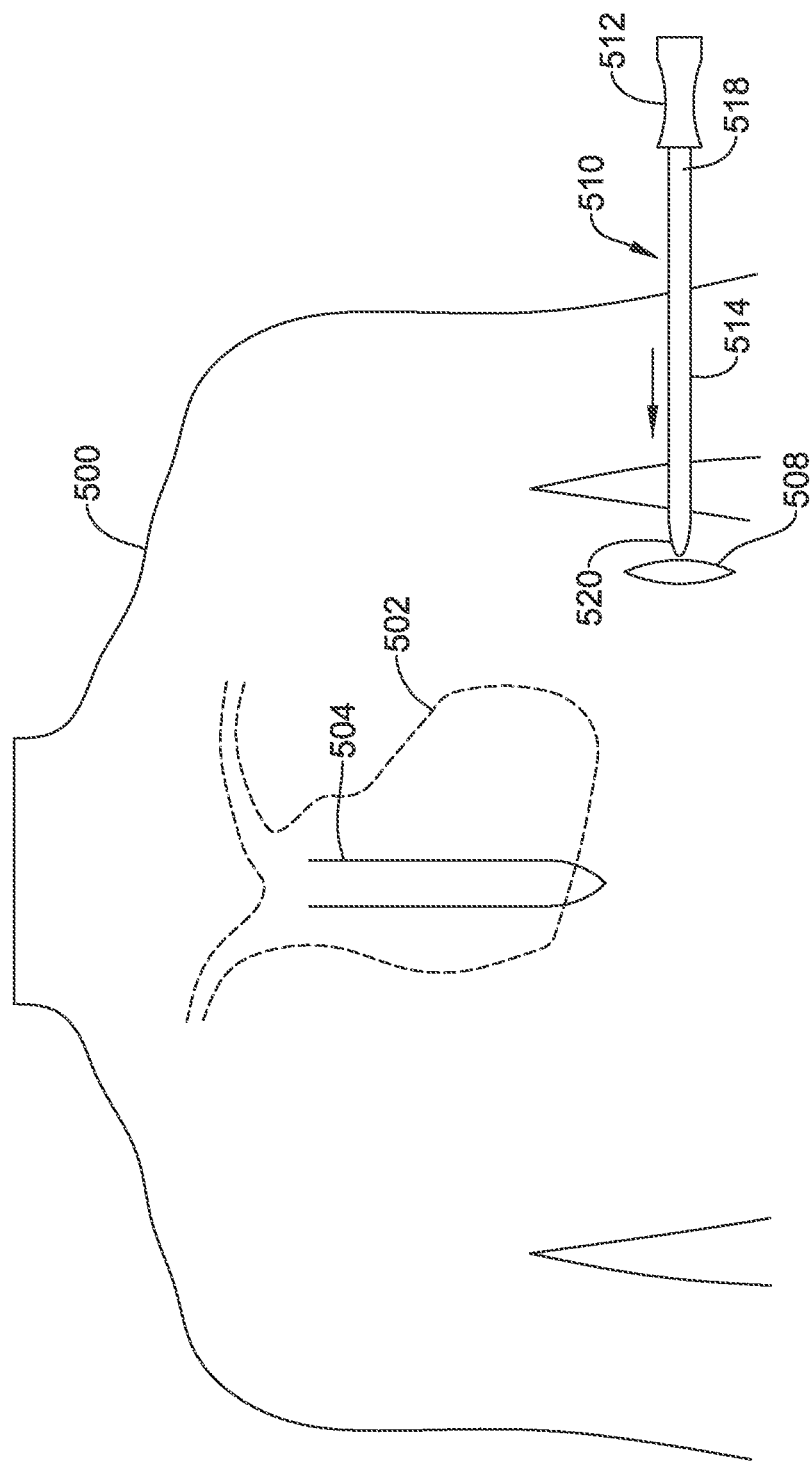
FIGS. 5A-5C illustrate a first method for implanting an implantable medical device.
Figure 5B:
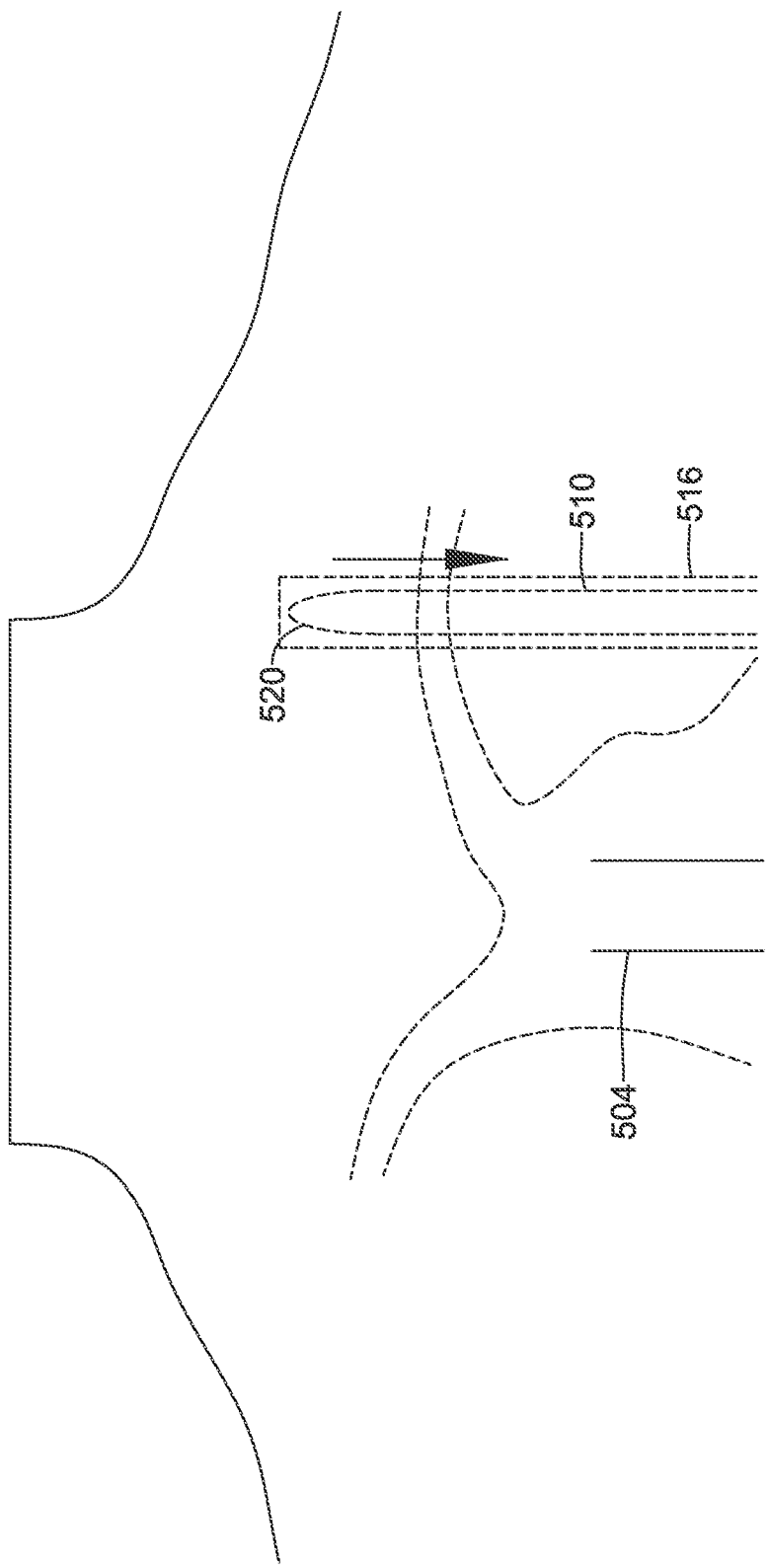
Figure 5C:
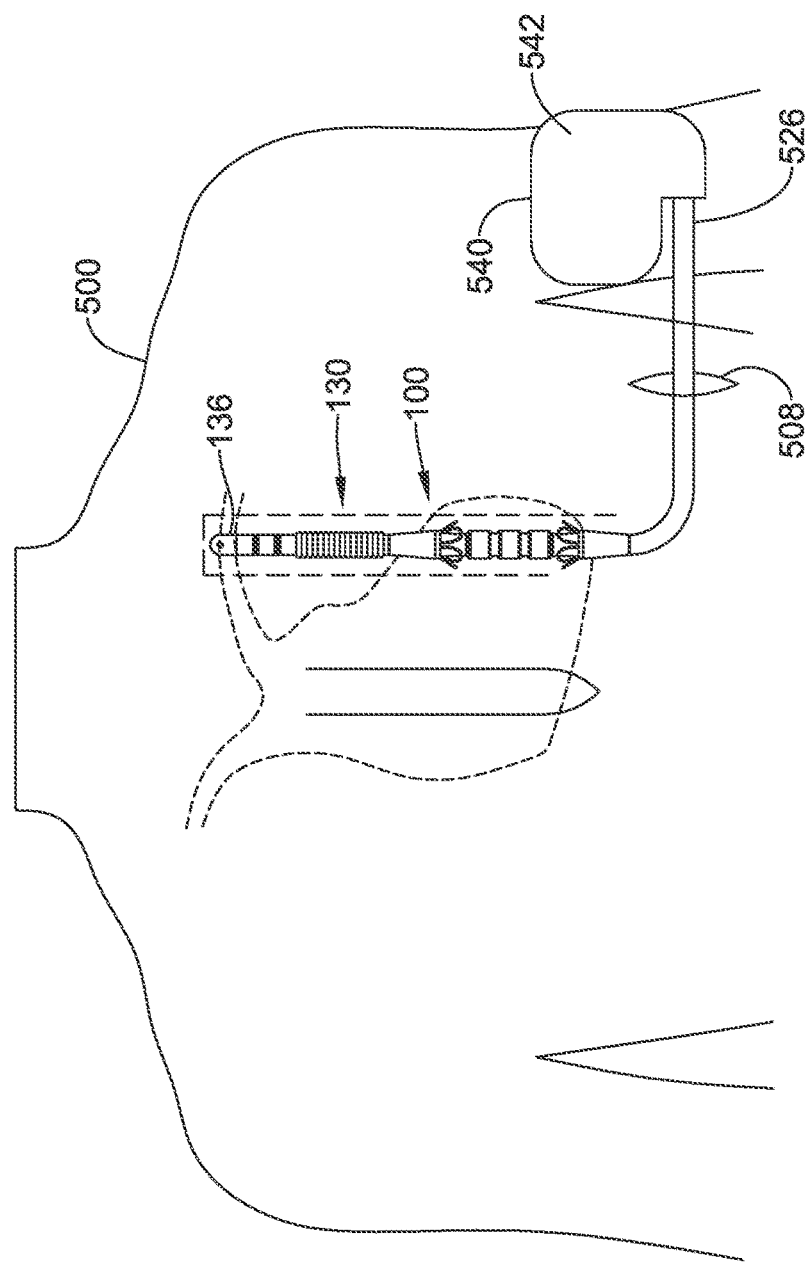

FIGS. 5A-5C depict an illustrative method of implanting an implantable medical device (IMD) in a patient 500. In some cases, the implantable lead 130, having the retention device 100 disposed thereon, may be used. Beginning with FIG. 5A, certain anatomy of the patient 500 is highlighted including a heart 502 and sternum 504. An axillary incision may be made near the left axilla of the patient 500, as shown at 508. An insertion tool 510 may be used in the procedure. The insertion tool 510 may have a handle 512 at a proximal end 518, and an elongate shaft 514 extends distally from the handle 512 toward a distal dissecting tip 520. The distal tip 520 may be shaped for dissection of subcutaneous tissue. In one example, the distal tip 520 has a tapered blunt tip, allowing for passage by dissection through subcutaneous tissue without encouraging piercing through the epidermis.

A channel(s) may optionally be provided in the insertion tool 510 to allow infusion of fluids for antiseptic, anti-inflammatory, pain reduction, or other purposes at the dissecting tip or along the length thereof. If ingrowth or adhesion is desired, a tissue adhesive or steroid may be infused as well.

As shown by the arrow in FIG. 5A, the insertion tool 510 may be inserted through the axillary incision 508. In some cases, the insertion tool 510 may be deflectable or steerable and may be used to create a tunnel 516 from the axillary incision 508, just to the left of and superior of the xiphoid near the lower portion of the sternum 504, and advanced generally parallel to the sternum 504, as shown in FIG. 5B. In an example, the insertion tool 510 is advanced as shown with an introducer sheath thereon. The insertion tool 510 may then be withdrawn, keeping the introducer sheath in place.

In some cases, the lead 130 may be prepared for use by applying the retention device 100 thereon at a desired location such as by sliding the retention device 100 over the proximal or distal end of the lead 130. The retention device 100 may be secured onto the lead 130 by tightening a suture thereon. Alternatively, the lead 130 may be provided by the manufacturer with the retention device 100 pre-attached and bonded to the lead 130, such as by using an adhesive, welding, heating, shrinking, or co-manufacturing process such as insert molding. The retention device 100 may include a longitudinal slit to allow lateral placement onto a lead, if desired. In some examples, a sheath may be placed over the lead 130 and retention device 100 to aid in holding the retention device 100 at the desired location on the lead, and to hold the securing mechanisms of the retention device in a delivery configuration, preventing them from engaging tissue during implantation prior to reaching a desired implant position.

As shown in FIG. 5C, the lead 130 may be positioned at a desired location in the tunnel 516 by insertion through the introducer sheath. Removal of the introducer sheath and the sheath placed over the lead 130 (if one is used) then allows the retention device 100 to become engaged to the patient tissue at a desired location as the securing mechanisms on the retention device 100 expand from the delivery configuration to a deployed configuration. At the end of this step or prior to this step, a proximal plug 526 of the lead 130 may be located relatively near the axillary incision 508, though this may depend on the anatomy of the patient 500 and the length of the lead 130. In some cases, the proximal plug or connector 526 of the lead 130 may be attached to an implantable canister 540. In some cases, the lead 130 coupled to the canister may comprise the IMD.

The canister 540 may include a housing 542 to house operational circuitry. For a cardiac electrical stimulus device, the operational circuitry may couple to the electrodes on the lead via conductors and be configured to analyze biological signals and deliver output therapy in the form of at least one of bradycardia pacing, anti-tachycardia pacing, cardiac resynchronization therapy, or defibrillation, using the electrodes on the lead 130. In other examples, non-cardiac therapy and/or stimulus may be provided such as by having a drug infusion pump as the canister 540 for infusing a drug or other substance for example for diabetes or pain management, and/or by having a neuromodulation or neurostimulation device adapted to deliver electrical stimuli to a desired body part to induce, modulate, or block signals and/or activities; for example, spinal cord stimulation may be applied to alleviate or block pain, or vagus nerve stimulation may be applied to address various conditions.

In some cases, the canister 540 may then be implanted through the axillary incision 508 and sutured to the patient 500 tissue. Having the IMD (including the lead 130) implanted with the retention device 100 may provide several potential benefits. For instance, the retention device 100 may improve stability during implantation of the lead 130. The retention device 100 may also improve stability during acute implant duration, prior to tissue ingrowth. In some cases, the retention device 100 may potentially improve long term stability, including a chance for less noise due to electrode movement and reduced inappropriate shocking. In some cases, the retention device 100 may eliminate the need for suturing the lead down to the patient fascia. That is, a physician may implant the device without suturing the retention device 100 to the patient, instead relying on the securing mechanisms thereof to hold it in place.

Several modifications may be made to the method of implanting the IMD described in FIGS. 5A-5C. For example, rather than the steps of FIGS. 5A-5C to place the lead 130 over the ribs and alongside the sternum, a substernal approach may be taken by advancing the lead beneath the ribs. The lead may be directed to an entirely different location, such as near the spine, kidney, or elsewhere. The canister 540 may be placed elsewhere as well, such as in the abdomen, near or in the buttocks, or adjacent or near the clavicle, or any other desired position.

In some cases, several alternative structures for leads and retention devices may be used and additional steps/features may be are provided. In some examples, the retention device may take the form of the retention devices 200 or 400. For instance, in the case where the retention device 400 is used, the steps of positioning the lead at a desired location in the tunnel 516 and removing of the introducer sheath and the sheath placed over the lead 130 may be similar to the steps described above. Additionally, the first ends of the securing mechanisms 404A and 404B may be moved, slid, and/or shifted along the elongate body 402 of the retention device 400 towards the second ends into the recesses 422A and 422B. Accordingly, the intermediate section may curve, crimp, fold, and/or compress such that the intermediate section moves away radially from the elongate body 402 into the deployed configuration. Furthermore, since both ends of the securing mechanisms 404A and 404B reside in the recesses 422A and 422B, the securing mechanisms 404A and 404B may be held in the deployed configuration by the ledges of the recesses and secure the lead 130 to the tissue of the patient.

FIGS. 6A-6E depict another illustrative method of implanting an IMD in the patient 500. Similar to the method shown in FIGS. 5A-5C, the implantable lead 130, having the retention device 100 disposed thereon, may be used. Beginning with FIG. 6A, a xiphoid incision 606 may be made just to the left of and superior of the xiphoid near the lower portion of the sternum 504, and an axillary incision may be made near the left axilla of the patient 500, as shown at 508. An insertion tool 610 may be used in the procedure. The insertion tool 610 may have a handle 612 at a proximal end 618, and an elongate shaft 614 extends distally from the handle 612 toward a distal dissecting tip 620 that includes an attachment feature 616. The attachment feature 616 is shown as a suture opening, however, other suitable attachment features known in the art may be used. The distal tip 620 may be shaped for dissection of subcutaneous tissue. In one example, the distal tip 620 has a tapered blunt tip, allowing for passage by dissection through subcutaneous tissue without encouraging piercing through the epidermis. A channel (s) may be provided in the insertion tool 610 to allow infusion of fluids for antiseptic, anti-inflammatory, pain reduction, or other purposes at the dissecting tip or along the length thereof. If ingrowth or adhesion is desired, a tissue adhesive or steroid may be infused as well. As shown by the arrow in FIG. 6A, the insertion tool 610 may be inserted through the xiphoid incision 606 and advanced toward the axillary incision 508.

Figure 6A:
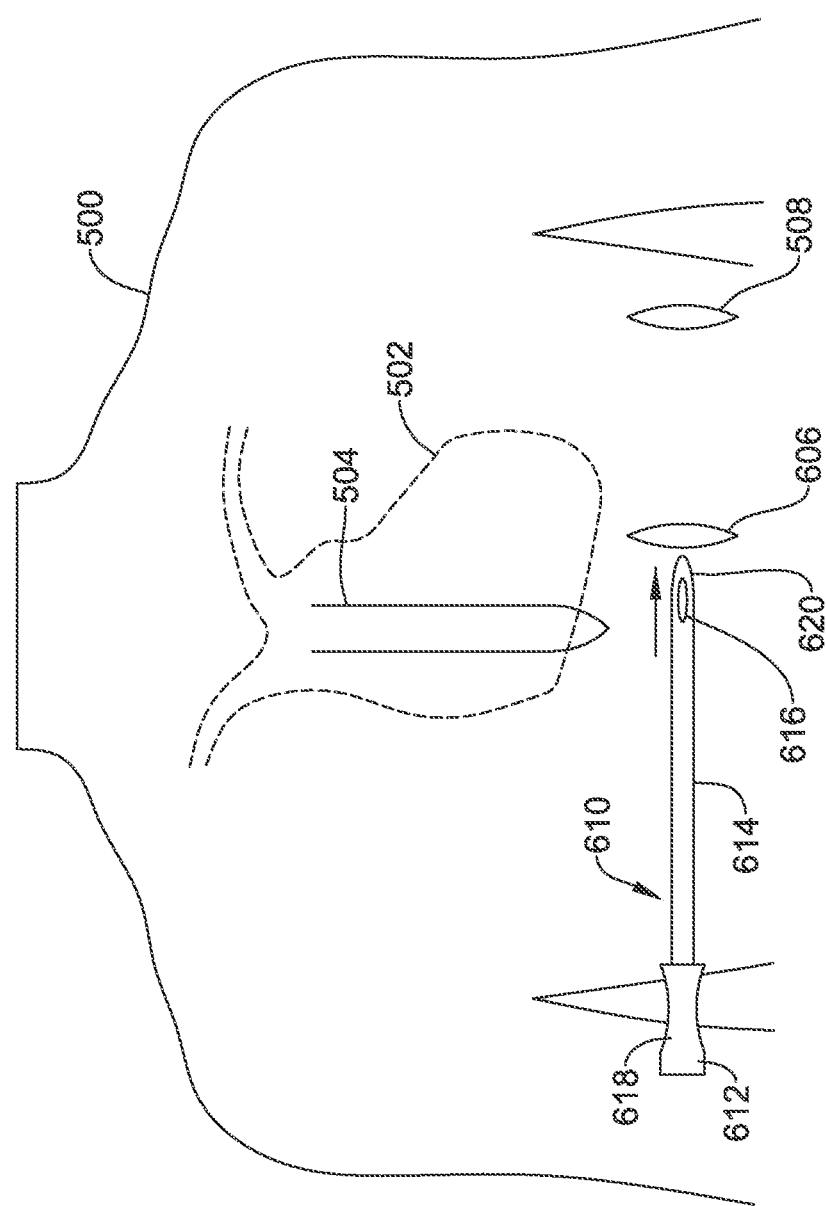
FIGS. 6A-6E illustrate a second method for implanting the implantable medical device.
Figure 6B:
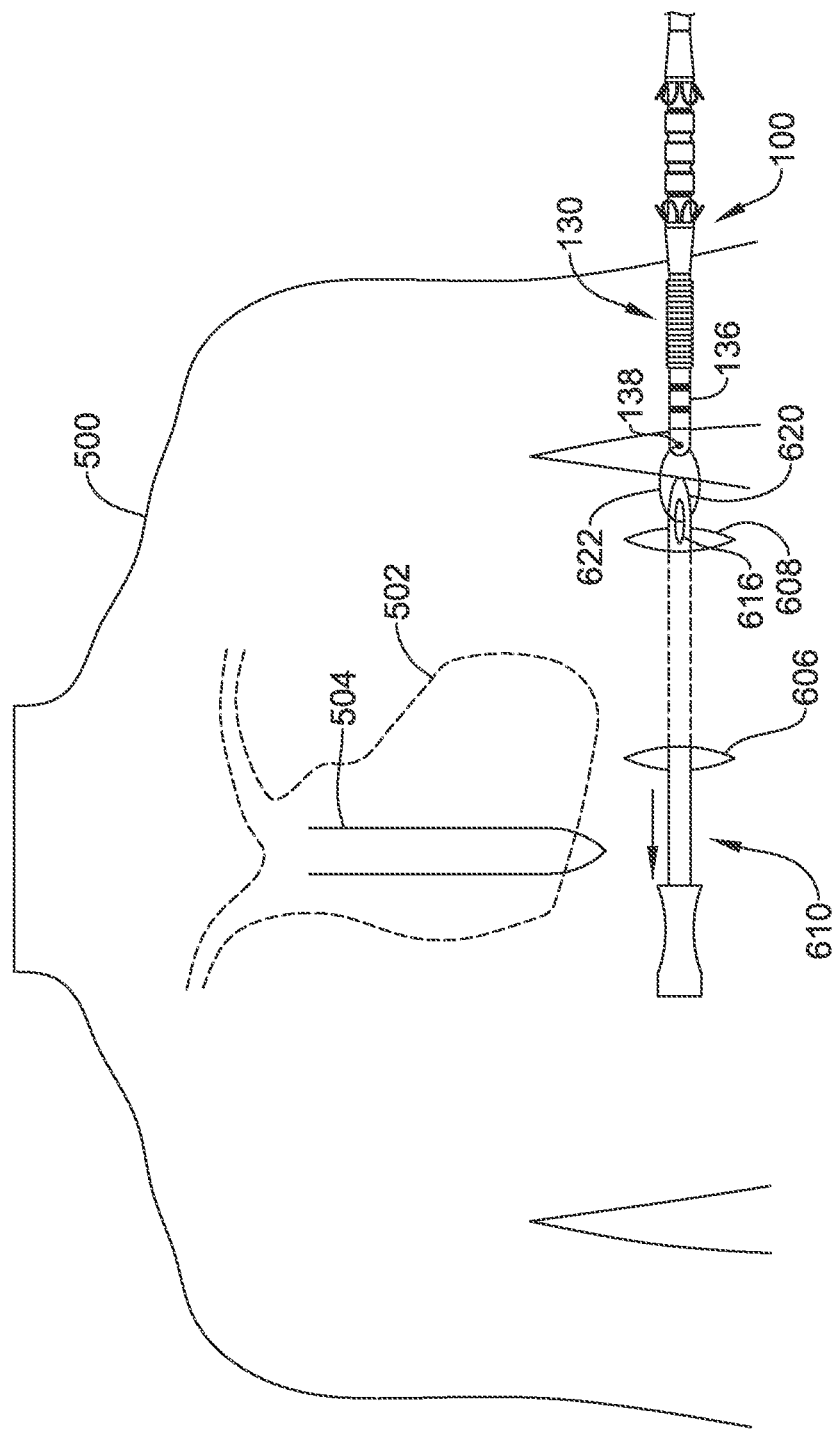

As shown in FIG. 6B, the lead 130 may be prepared similar to the description above in regard to FIGS. 5A-5C. In some cases, the insertion tool 610 may be inserted into the xiphoid incision 606 until its distal tip 620, including the attachment feature 616, can be accessed through the axillary incision 508. Then the suture 622 may be used to attach the attachment feature 616 of the insertion tool 610 to an attachment feature 138 on a distal tip portion 136 of the lead 130. If needed, the lead 130 may be prepared by attaching a retention device 100 (before or after attachment to the insertion tool 610). Alternatively, the retention device 100 may be permanently attached to the lead 130 during manufacturing thereof.

Figure 6C:
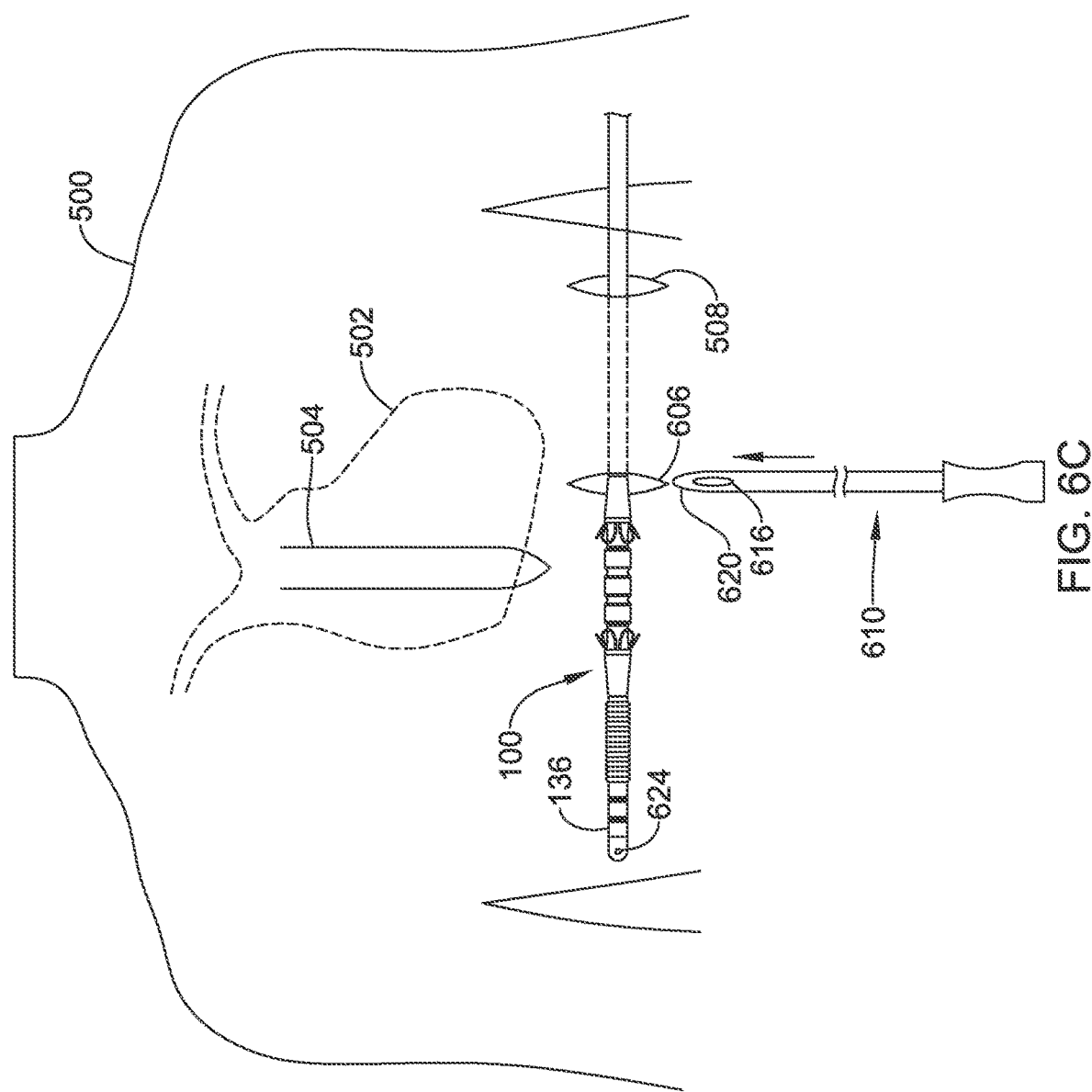

In some examples, a sheath may be placed on the lead, either at the time of surgery or as a preloaded system, to prevent the retention device 100 engaging tissue during its introduction into the patient. Next, the insertion tool 610 may be withdrawn through the xiphoid incision 606, with the suture 622 pulling the lead 130 into the patient's 500 subcutaneous tissue through the axillary incision 508. Alternatively, a sheath may be used to advance the lead 130 into tissue without the use of the suture to pull the lead 130. The end of this pulling step is shown in FIG. 6C, where the attachment feature 138 at the distal tip portion 136 of the lead 130 extends through the xiphoid incision 606 and forceps (not shown) may be used to grasp the suture 622, which may be cut from the attachment feature 616. At the end of this step, the proximal plug 626 of the lead 130 may be located relatively near the axillary incision 508.

If used, a sheath may be removed after the lead has been pulled to and through the axillary incision. Alternatively, the sheath may be kept in place until implantation is complete. In still other alternatives, no sheath is used during this tunneling and pulling step. For example, no sheath may be needed during pulling from the axillary incision to the xiphoid incision if the securing mechanisms are biased to allow passage through tissue in one direction but not the other.

Figure 6D:
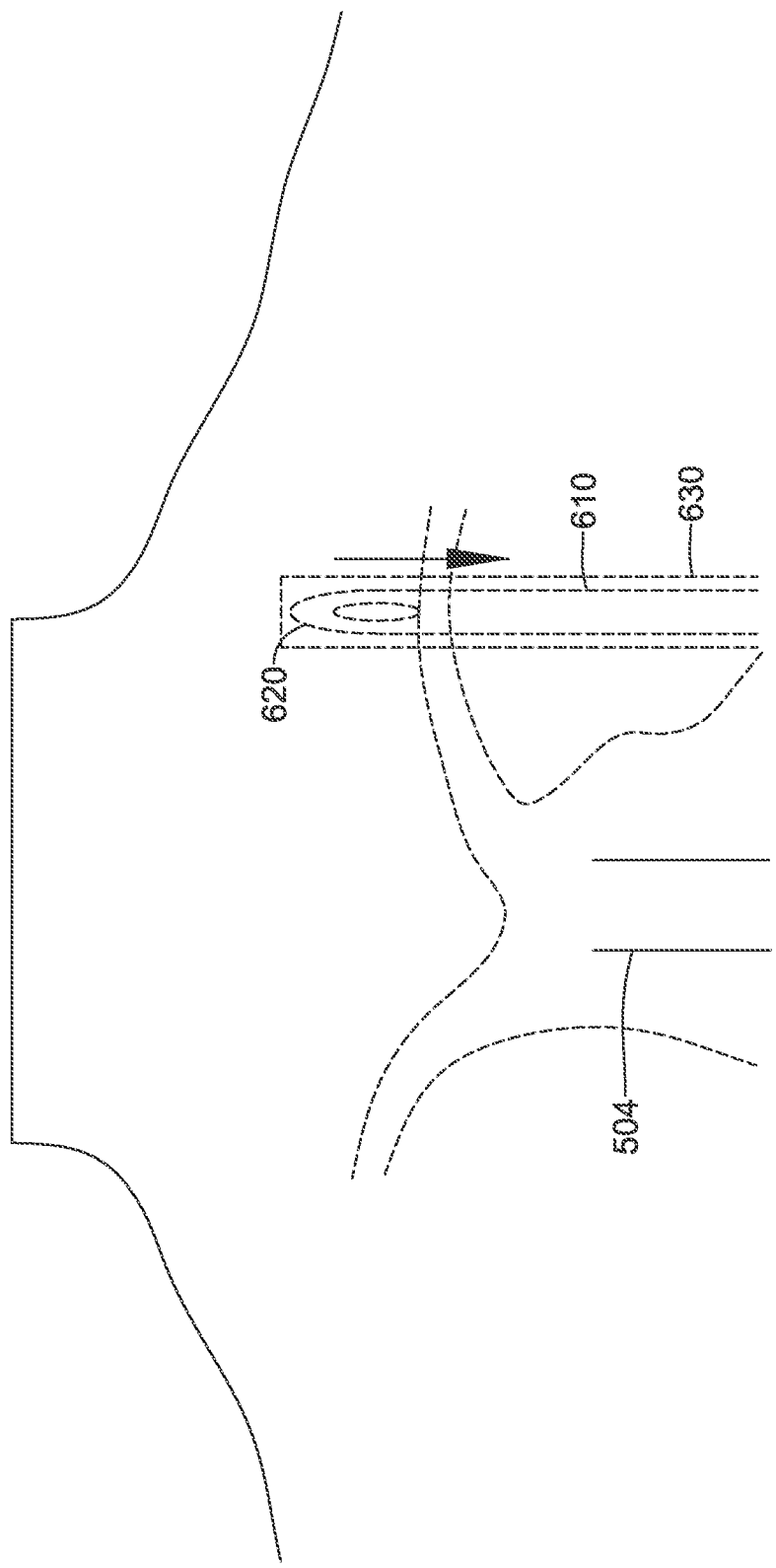

In the example shown in FIG. 6C and as described herein, the distal tip 620 of the insertion tool 610 may be shaped to allow for passage by dissection through subcutaneous tissue. Accordingly, the insertion tool 610 may be reinserted into the xiphoid incision 606 and advanced generally parallel to the sternum 504 to create a tunnel 630, as shown in FIG. 6D. Though not shown, an introducer sheath may be placed over the insertion tool 610 during the step shown in FIGS. 6C-6D. The insertion tool 610 may then be withdrawn, with the introducer sheath left in place.

Figure 6E:
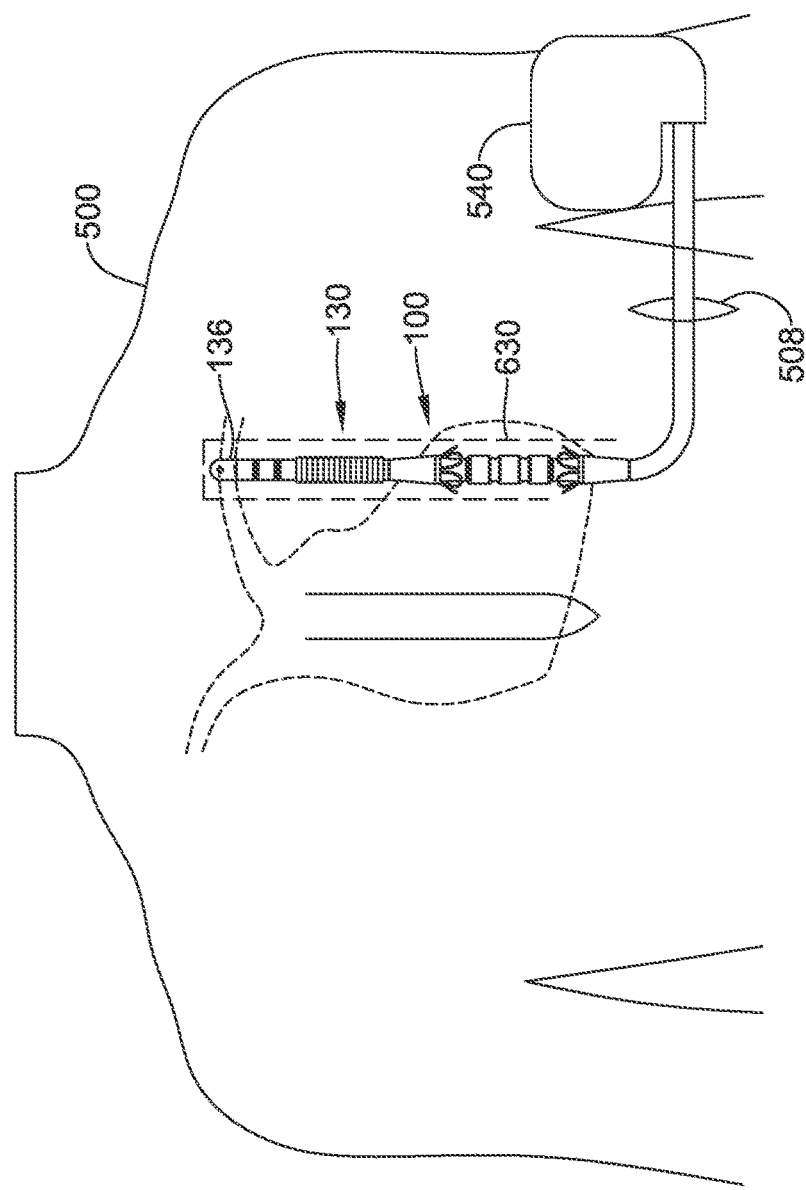

As shown in FIG. 6E, the lead 130 may be reinserted into the xiphoid incision 606 and advanced generally through the tunnel 630 and retained introducer sheath. The introducer sheath is then split and removed over the lead. Removal of the introducer sheath then allows the retention device 100 to become engaged to the patient tissue at a desired location as the securing mechanisms on the retention device 100 expand from the delivery configuration to a deployed configuration. Furthermore, in some cases, a suture may be placed in a recess of the retention device 100 and the lead 130 may be sutured to the fascia to further secure the lead 130 inside the patient 500.

In some examples, the xiphoid incision 606 may be accessed to place the suture in the recess of the retention device 100. If the introducer sheath is used in both passage through the axillary-xiphoid tunnel and in the parasternal tunnel, it would be removed at the left axilla. If the introducer sheath is used only in the parasternal tunnel, or is removed after the passage from axilla to xiphoid and a second introducer sheath used for the parasternal tunnel, then the introducer sheath would be removed at the xiphoid. The proximal plug 526 of the lead 130 may then be attached to the canister 540 and the canister 540 may be implanted through the axillary incision 508 and sutured to the patient 500 tissue.

The two incision technique shown in FIGS. 6A-6E may be generally similar, except with respect to the use of the retention device, to certain examples in U.S. Pat. No. 7,655,014, titled APPARATUS AND METHOD FOR SUBCUTANEOUS ELECTRODE INSERTION, the disclosure of which is incorporated herein by reference.

Figure 7A:
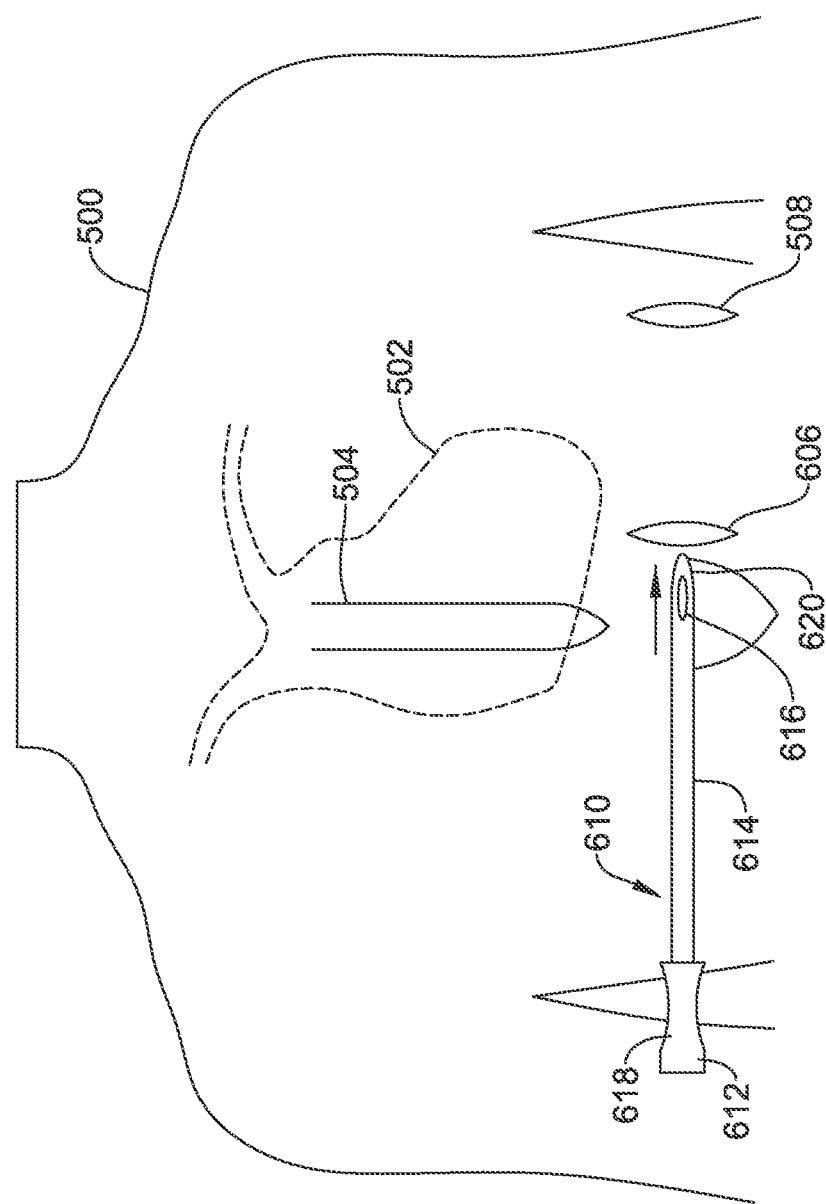
Figure 7B:
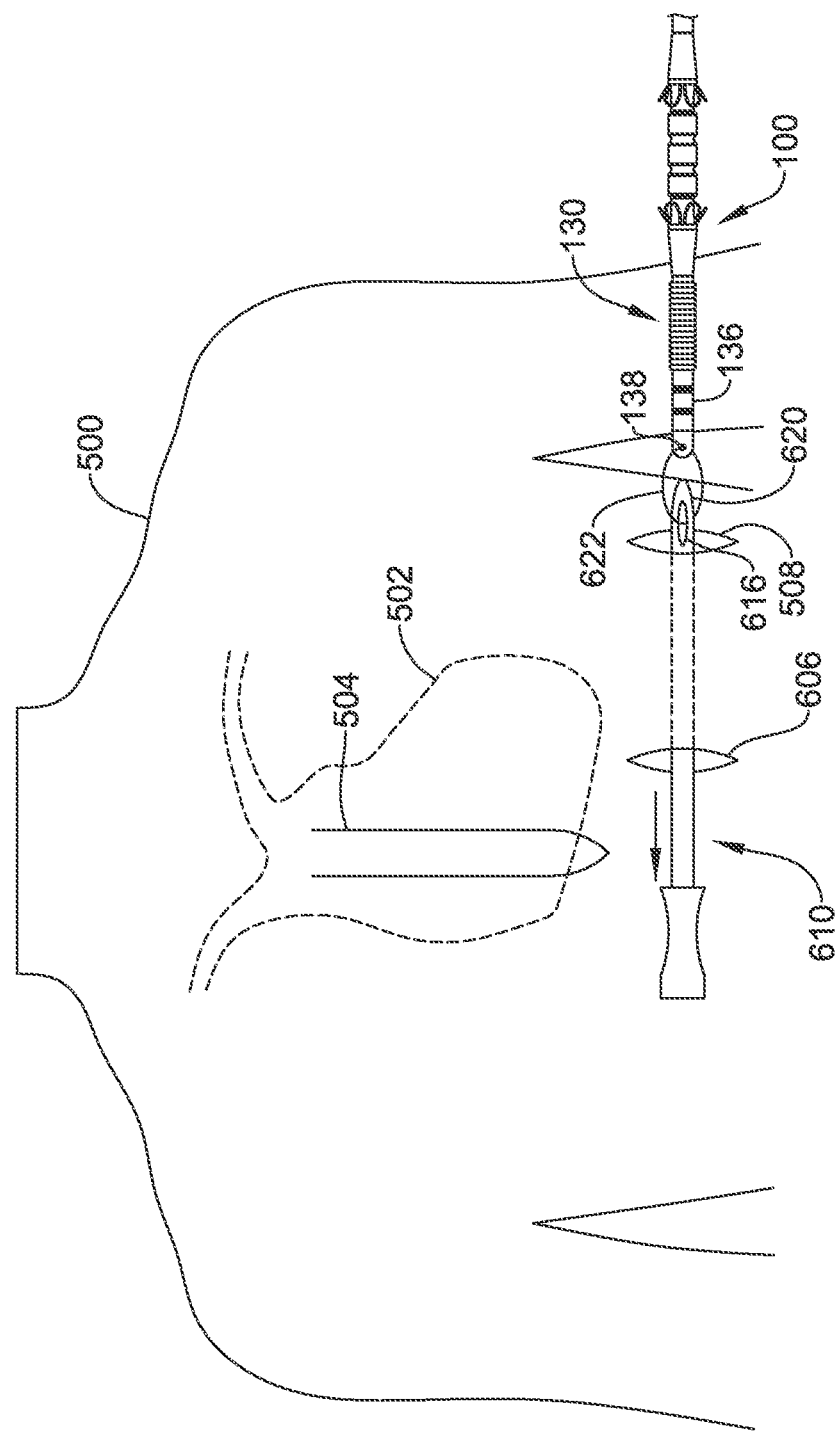
Figure 7C:
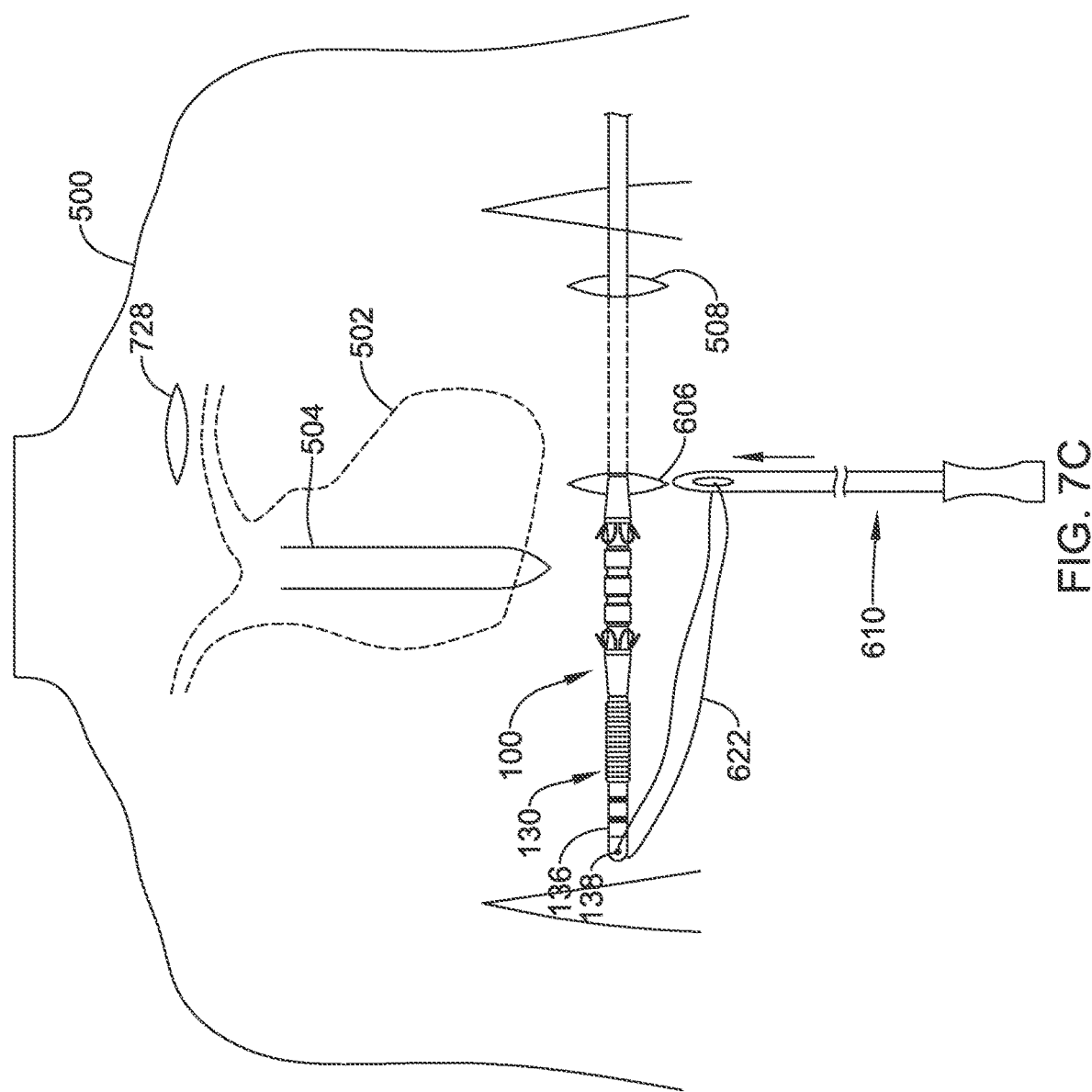

FIGS. 7A-7F depict another illustrative method of implanting an IMD in the patient 500. Similar to the method shown in FIGS. 5A-5C, the implantable lead 130, having the retention device 100 disposed thereon, may be used. The beginning of this method may be similar to the method depicted in FIGS. 6A-6B. As shown in FIG. 7A, the xiphoid incision 606 and the axillary incision 508 are made. The insertion tool 610 may then be inserted through the xiphoid incision 606 and advanced toward the axillary incision 508. Then a suture 622 may be used to attach the attachment feature 616 of the insertion tool 610 to the attachment feature 138 on the distal tip portion 136 of the lead 130. Next, the insertion tool 610 may be withdrawn through the xiphoid incision 606, with the suture 622 pulling the lead 130 into the patient's 600 subcutaneous tissue through the axillary incision 508. The end of this pulling step is shown in FIG. 7C, where the attachment feature 138 at the distal tip portion 136 of the lead 130 extends through the xiphoid incision 606. At the end of this step, a proximal plug 626 of the lead 130 may be located relatively near the axillary incision 608.

In the example shown in FIG. 7C, the suture 622 remains attached to the insertion tool 610, which is shown in alignment with the sternum 504 in preparation for the next step of the procedure. An upper incision 728 may be made a short distance to the left of the sternum 504 at a location that is superior to the xiphoid incision 606, approximately along the left sternal margin. For example, the upper incision 728 may be located approximately 8 to 18 cm superior of the xiphoid incision 606, and 1-3 cm left of the sternum 504. The upper incision 728 may also be described as level with or inferior to the manubrium and/or level with or superior to the atria of the heart. These particular locations are illustrative and not required; various implant locations can be used. The insertion tool 610 may then be reinserted into the xiphoid incision and advanced generally parallel to the sternum 504 toward and through the upper incision 728.

Figure 7D:
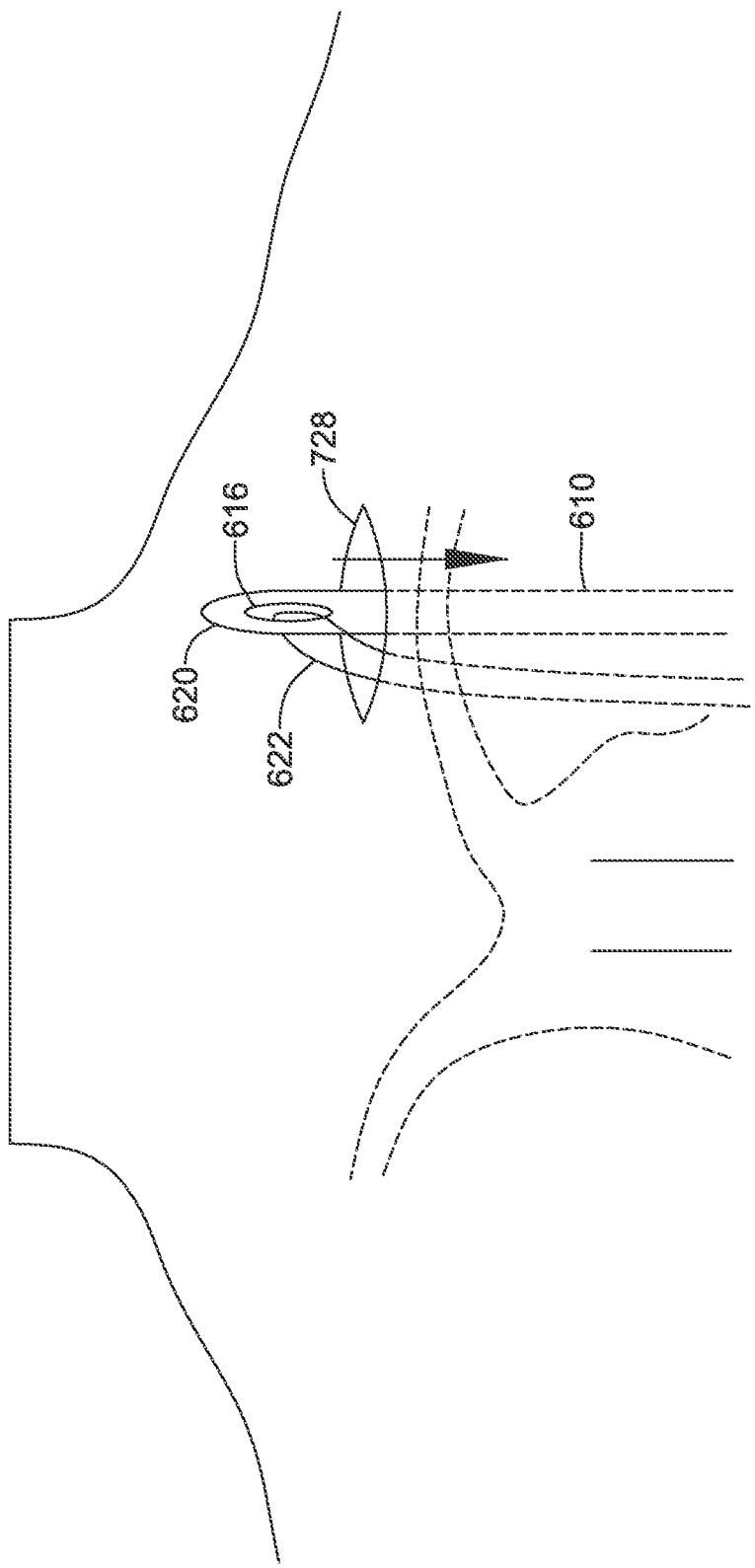
Figure 7F:
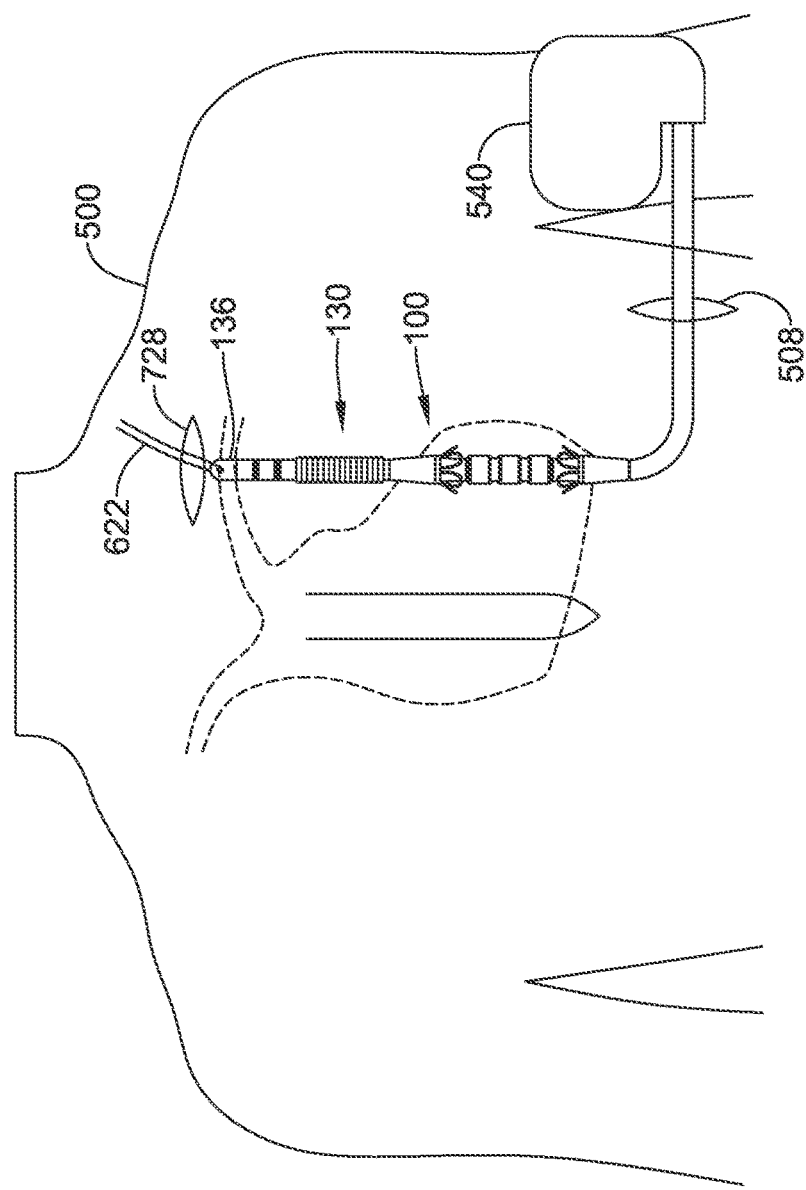

Turning to FIG. 7D, the distal tip 620 of the insertion tool 610 extends out of the upper incision 728 until the attachment feature 616 can be accessed. Next, a forceps (not shown) may be used to grasp the suture 622, which may be cut from the attachment feature 616. The insertion tool 610 may then be withdrawn. Turning to FIG. 7E, the forceps (not shown) may be used to pull the suture 622 through the upper incision 728, drawing the lead 130 through the xiphoid incision 606 into the patient 500 and through the tunnel formed by the insertion tool 610. The suture 622 may be pulled until the lead 130 achieves the position shown in FIG. 7F, where the distal tip portion 136 of the lead 130 and its attachment feature 138 may be accessed at the upper incision 728 and the proximal plug 526 of the lead 130 may be attached to a canister 540. The canister 540 may then be implanted through the axillary incision 508 and sutured to the patient 500 tissue.

In addition, in some cases, when an introducer sheath (not shown) is used to compress the securing mechanisms into the delivery configuration, the sheath may be removed or withdrawn and the securing mechanisms may expand or extend into its deployed configuration to engage, push against, and/or anchor the lead 130 to the patient 500 tissue (e.g. the tunnel formed by the insertion tool 610). Furthermore, in some cases, a suture may be placed in a recess of the retention device 100 and the lead 130 may be sutured to the fascia to further secure the lead 130 inside the patient 500. In some examples, the xiphoid incision 606 may be accessed to place the suture in the recess of the retention device 100.

In the various examples, shown, the end location for the retention device 100 may be in several different spots. In some examples, the retention device 100 will be placed at the distal end of the lead and will engage tissue more or less near the sternum superior to one or more electrodes of the lead 130. In other examples, the retention device 100 will end up near the xiphoid process, inferior to the anatomical position of the electrodes on the lead 130. In other examples, the retention device 100 may be positioned along the inframammary crease.

As shown above, three general implantation methods are shown. Various alternatives to steps and devices shown are identified. At a high level, a three incision technique is shown with a sternal incision, a xiphoid incision, and an axillary incision, wherein one or two sheaths may be used to pass a lead having an anchoring device thereon through one or more of the axilla-xiphoid tunnel or the parasternal tunnel, wherein the sheath may be provided to perform one or more of supporting the lead passage, maintaining a tunnel for lead insertion, and/or to restrain or retain securing mechanisms on the lead. In the three incision technique, the present invention provides options that reduce the suturing at the xiphoid incision and/or which increase the anchoring strength at the xiphoid incision.

At a high level, a two incision technique is shown that omits the sternal incision of the three incision technique; a sheath is used to secure the parasternal tunnel and may additionally serve to support lead passage and/or to restrain or retain securing mechanisms on the lead. In the two incision technique, the present invention again provides options that may reduce the suturing at the xiphoid incision and/or which increase the anchoring strength at the xiphoid incision.

At a high level, a single incision method may omit each of the xiphoid and sternal incisions; a sheath is used to secure the parasternal tunnel and may additionally serve to support lead passage and/or to restrain or retain securing mechanisms on the lead. The present invention, for the single incision method, aids omission of at least the xiphoid incision by providing anchoring at a desired location on the lead. The single incision method may use a curved, telescoping and/or deflecting or steerable tunneling system, such as in US PG Pat. Pub. No. 20170020551, titled MINIMALLY INVASIVE METHOD TO IMPLANT A SUBCUTANEOUS ELECTRODE, the disclosure of which is incorporated herein by reference. A single incision method may also or instead use a method as shown in U.S. patent application Ser. No. 16/104,250, titled SINGLE INCISION SUBCUTANEOUS IMPLANTABLE DEFIBRILLATION SYSTEM, the disclosure of which is incorporated herein by reference.

As illustrated in these examples, the present invention facilitates flexibility in selection of the implant procedure. For example, with a very active or young patient where lead migration is a great concern, or for a patient with a lot of adipose tissue that may make lead anchoring more challenging, a multiple incision technique may be performed using both suturing techniques and the retention device to hold the lead in place by multiple approaches. For other patients, a single incision technique may be used relying solely on the retention device, or a two incision technique that omits a xiphoid incision relying on an intermediate fixation point as well as, optionally, distal tip fixation. The physician has the option of distal tip fixation, and intermediate suture-based fixation in addition to relying on the retention device 100. Such flexibility may allow the physician to make changes to the planned procedure intraoperatively, without having to discard a lead that is deemed unsuitable to the particular patient. A physician may determine, through gentle tugging at the proximal (or distal) end of the lead, whether sutures need to be applied.

Figure 8:
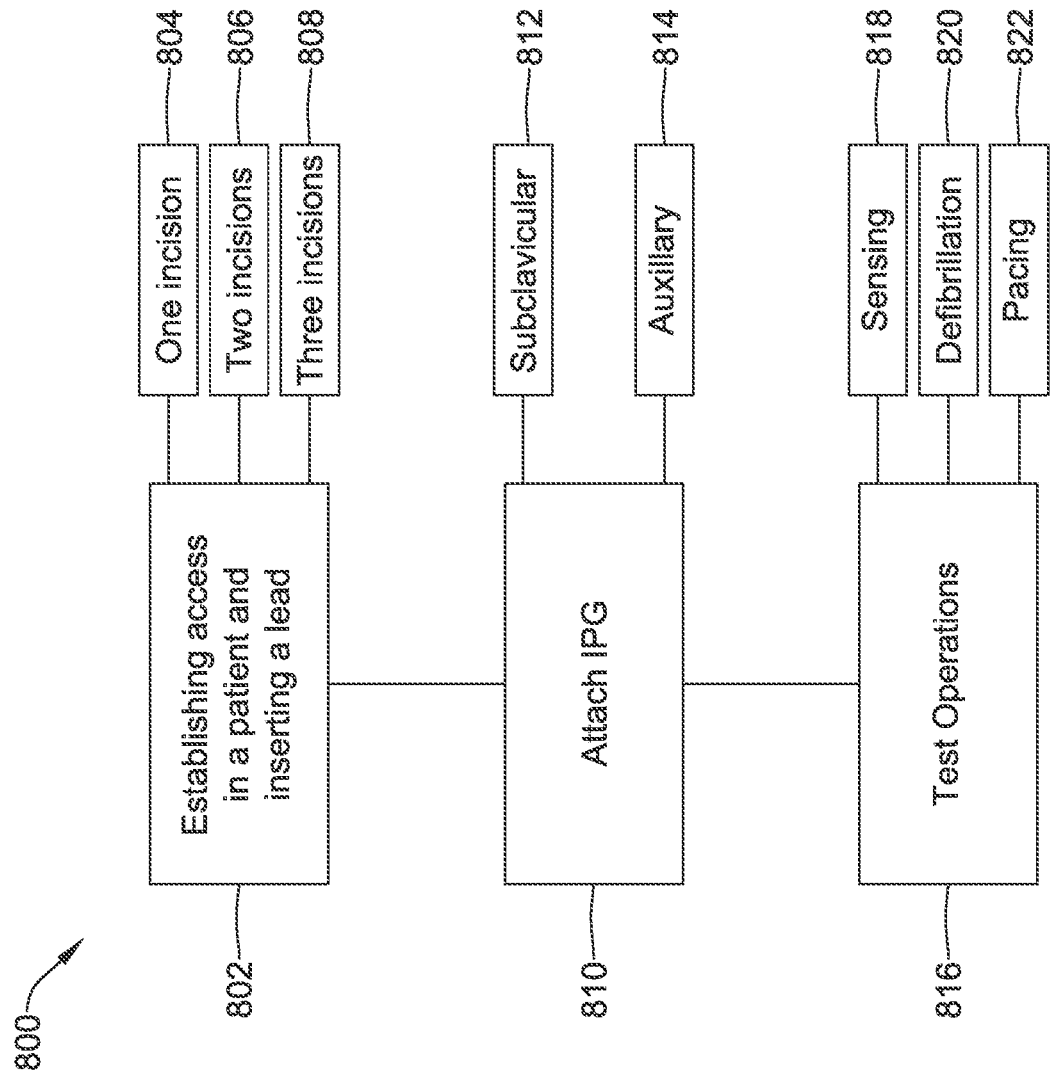
FIG. 8 is a block flow diagram for an illustrative method.

FIG. 8 is a block flow diagram of an illustrative method 800 for providing an IMD system to a patient. As shown, the method 800 comprises establishing access in a patient and inserting a lead 802, attaching an implantable pulse generator (IPG) to the lead 810, and performing test operations 816. The IPG may also be referred to herein as a canister or implantable canister.

For example, establishing access to the patient and inserting a lead 802 may include using a one incision implantation method, such as described above relative to FIGS. 5A-5C as indicated at 804. In another example, establishing access to the patient and inserting a lead 802 may include using a two incision implantation method 806, generally as shown above relative to FIGS. 6A-6E. In another example, a three incision implantation method 808, such as described above relative to FIGS. 7A-7F.

Regardless of the incision method used, once the lead is at a selected position or configuration in the patient, securing mechanisms located on a retention device of the lead may engage, push against, and/or anchor the lead to the patient tissue. Suturing to the fascia may thus be reduced or omitted.

In an example, attaching an IPG to the lead 810 may include attaching to a canister located in a subclavicular location 812, historically a common place to put an implanted canister for a transvenous defibrillator or pacemaker. In another example, attaching to an IPG may include attaching to a canister located in an axillary position 814, such as that used with the S-ICD System. Other IPG locations may be used. Attachment may be directly to the IPG or to a splitter, yoke, or lead extension, if desired.

In an example, test operations 816 may be used to verify one or both of device functionality and efficacy. For example, sensing operations 818 may be tested and configured to check for adequate signal availability, for example, or by setting gain, filtering, or sensing vector selection parameters. Defibrillation operations 820 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 820 may include determining for a given patient an appropriate defibrillation threshold, and setting a parameter for therapy delivery at some safety margin above the defibrillation threshold. For other, non-cardiac-electrical systems, (such as a drug pump or neuromodulation system), other therapy testing regiments may be applied, as is convention for those other products.

In an example, pacing testing operation 822 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

As noted above, the illustrative retention devices may be formed of any biocompatible material. Some examples include elastic, biocompatible alloys capable of forming stress induced martensite (SIM). Nitinol (TiNi) is an example of such materials. A retention device may be formed from stainless steel, such as high tensile stainless steel, or other materials, including metals and metal alloys, such as tungsten, gold, titanium, silver, copper, platinum, palladium, iridium, ELGILOY nickel-cobalt alloys, cobalt chrome alloys, molybdenum tungsten alloys, tantalum alloys, titanium alloys, etc. A retention device may be formed from a lubricious polymer, such as a fluorocarbon (e.g., polytetrafluoroethylene (PTFE)), a polyamide (e.g., nylon), a polyolefin, a polyimide, or the like). A retention device may be formed of polyethylene, polyvinyl chloride (PVC), ethyl vinyl acetate (EVA), polyethylene terephthalate (PET), and their mixtures and copolymers. Another useful class of polymers is thermoplastic elastomers, including those containing polyesters as components. A retention device may also be comprised of such materials as soft thermoplastic material, polyurethanes, silicone rubbers, nylons, polyethylenes, fluorinated hydrocarbon polymers, and the like. A retention device may also be of a member selected from a more flexible material such as low density polyethylene (LDPE), polyvinylchloride, THV, etc. Still in further embodiments, a retention device may be composed of a combination of several these materials. In certain embodiments, a retention device may be formed of, impregnated with, or comprise a maker made of a radiopaque material such as, for example and without limitation barium sulfate ($BaSO4$), bismuth trioxide ($Bi2O3$), bismuth subcarbonate ($Bi2O2CO3$), bismuth oxychloride (BiOCl), and tungsten.

Retention devices may be formed by molding, such as injection molding, or insert molding. In some examples, different parts or layers may be included such as by, for example, extruding a core tube having one or a plurality of layers (such as a lubricious inner layer with a tie layer thereon to allow ready attachment of additional material) of the retention device and insert molding an outer surface thereon of a different material, with the securing mechanisms added via the insert molding process. In another example, a wire member may be used as a starting point for an insert molding process, wherein the wire member comprises a set of tines to use as securing mechanisms on which a polymeric material is added.

Lead structures for use with the present invention may take any suitable type and use any suitable material, such as the materials noted above. Internal longitudinal or lateral support members, such as braids, core wires, etc. may be provided. Extrusion or molding may be used for lead manufacture. Internal conductors in the lead may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The lead may include on all or a portion thereof various coatings such as an anti-microbial coating to reduce the likelihood, severity, and/or progression of infection.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, some and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems. The present invention may be used for non-cardiac devices such as, for example and without limitation, the Precision Novi and Precision Spectra neuromodulation devices offered by Boston Scientific. Any suitable lead structure may be used, such as leads adapted for subcutaneous implantation for cardiac monitoring or therapy purposes, and/or leads adapted for use in spinal, deep brain, or peripheral neuromodulation systems such as vagus or sacral nerve therapies. When used in a neuromodulation system, the methods of FIG. 8 may be modified to swap out the test operations at 816 to determining appropriate therapy settings using methods well known in the neuromodulation field. The present invention may also be used in association with a drug pump that injects a fluid; rather than anchoring an electrical lead, a fluid injection catheter used by the drug pump may be implanted and anchored in place.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting an implantable lead in a patient comprising the use of an implantable lead having a first end for coupling to an implantable medical device and a second end for implantation at a target site in the patient, with a lead body extending therebetween and a retention device for use with an implantable medical device (IMD), the retention device comprising:
   an elongate body having a proximal end, a distal end, a hollow lumen extending from the proximal end to the distal end configured to receive a lead of the IMD, and an outer surface having a first recess configured to receive a suture for tying purposes to secure the retention device at a desired location on the lead; and
   one or more securing mechanisms each having a first end and a second end each coupled to the elongate body at a single longitudinal location on the elongate body, and an intermediate section between the first end and the second end configured to push against tissue of a patient;
   wherein the method comprises:
   inserting the implantable lead into the patient with the retention device placed on the lead at a desired location thereon and with a sheath disposed about at least a portion of the lead and compressing the one or more securing mechanisms of the retention device in a delivery configuration; and
   at least partly withdrawing the sheath such that the one or more securing mechanisms move to a deployed configuration to anchor the implantable lead to tissue of the patient.

2. The method of claim 1 wherein the step of inserting the implantable lead is performed by making a single incision, advancing an insertion tool having the sheath thereon through the incision and to a selected position in the patient, removing the insertion tool while keeping the sheath in place, and then inserting the implantable lead into the sheath such that the sheath compresses the one or more securing mechanisms of the retention device into the delivery configuration.

3. The method of claim 1 wherein the step of inserting the implantable lead is performed by:
   making a first incision and a second incision;
   making a first tunnel between the first and second incisions;
   making a second tunnel from the second incision to an end location; and passing at least the second end of the implantable lead through the second incision to the end location, wherein the step of inserting the implantable lead is performed such that the retention device is accessible near the second incision, and the method further comprises using a suture to anchor the retention device to the patient using the first recess to receive the suture at or near the second incision such that the one or more securing mechanisms and the suture are both used to secure the lead in the selected position.

4. The method of claim 1 wherein the step of inserting the implantable lead is performed by:
   making a first incision, a second incision and a third incision;
   making a first tunnel between the first and second incisions;
   making a second tunnel between the second and third incisions; and
   passing at least the second end of the lead through the second incision to the third incision, wherein the step of inserting the implantable lead is performed such that the retention device is accessible near the second incision, and the method further comprises using a suture to anchor the retention device to the patient using the recess to receive the suture at or near the second incision such that the one or more securing mechanisms and the suture are both used to secure the lead in the selected position.

5. The method of claim 1 wherein the intermediate section of each securing mechanism forms a loop defining an opening.

6. A retention device for use with an implantable medical device (IMD), the retention device comprising:
   an elongate body having a tapered proximal end, a tapered distal end, a hollow lumen extending from the proximal end to the distal end configured to receive a lead of the IMD, and an outer surface having a first recess;
   a first securing mechanism having first and second ends in the form of loops that encircle the elongate body and an intermediate section having first and second wires extending between the first end and the second end configured to push against tissue of the patient;
   wherein the retention device is configured to move between each of:
   a delivery configuration in which the first end of the first securing mechanism resides in the first recess, and the second end of the first securing mechanism resides over one of the tapered ends of the elongate body; and
   a deployed configuration in which each of the first and second ends of the first securing mechanism reside in the first recess;
   wherein the first end of the first securing mechanism is configured to slide toward the second end of the first securing mechanism to move the intermediate section of the first securing mechanism in a radial direction away from the elongate body to transition the retention device from the delivery configuration to the deployed configuration.

7. The retention device of claim 6 wherein when the intermediate section moves in the radial direction away from the elongate body, the intermediate section includes a curve.

8. The retention device of claim 6 wherein the first securing mechanism when in the delivery configuration, lies flat against the elongate body, and, when in the deployed configuration, the intermediate section extends radially out from the elongate body to serve as an anchor in tissue.

9. The retention device of claim 6 wherein the first and second ends of the first securing mechanism comprise wires that encircle the elongate body and the intermediate section includes two or more wires having first ends connected to the first end of the securing mechanism and second ends connected to the second end of the securing mechanism.

10. The retention device of claim 9 wherein the wires are nitinol wires.

11. An implantable medical device system comprising an implantable pulse generator comprising a canister housing operational circuitry adapted to generate a therapy output, a lead adapted for coupling to the implantable pulse generator and adapted to deliver the therapy output from the implantable pulse generator, and a retention device as in claim 6, wherein the lead is sized and shaped to be received in the hollow lumen of the retention device.

12. A combination retention device and lead for use in an implantable medical device system comprising:
   a lead having an elongate shaft with a first end adapted to couple to an implantable pulse generator and a second end adapted for implantation in a patient and having one or more electrodes thereon; and
   a retention device as in claim 6.

13. A method of implanting an implantable lead in a patient comprising the use of an implantable lead having a first end for coupling to an implantable medical device and a second end for implantation at a target site in the patient, with a lead body extending therebetween and a retention device adapted for placement on the lead body, wherein the retention device comprises:
   an elongate body having a proximal end, a distal end, a hollow lumen extending from the proximal end to the distal end configured to receive a portion of the lead, and an outer surface having a first recess; and
   a first securing mechanism having first and second ends configured to extend over and around at least a portion of the elongate body and an intermediate section between the first end and the second end configured to push against tissue of the patient, wherein the first recess is adapted to receive at least one end of the first securing mechanism; the method comprising:
   inserting the implantable lead into the patient with the retention device placed on the lead at a desired location thereon; and
   sliding the first end of the first securing mechanism toward the second end of the first securing mechanism causing the intermediate section of the first securing mechanisms to move radially away from the elongate body to a deployed configuration having a loop extending out from the elongate body to anchor the implantable lead to tissue of the patient.

14. The method of claim 13 wherein the step of inserting the implantable lead is performed by making a single incision, advancing an insertion tool having a sheath thereon through the incision and to a selected position in the patient, removing the insertion tool while keeping the sheath in place, and then inserting the implantable lead into the sheath with the retention device on the lead.

15. The method of claim 13 wherein the step of inserting the implantable lead is performed by:
   making a first incision and a second incision;
   making a first tunnel between the first and second incisions;
   making a second tunnel from the second incision to an end location; and
   passing at least the second end of the implantable lead through the second incision to the end location.

16. The method of claim 15 wherein the step of inserting the implantable lead is performed such that the retention device is accessible near the second incision, and the method further comprises using a suture to anchor the retention device to the patient at or near the second incision such that the first securing mechanism and the suture are both used to secure the lead in the selected position.

17. The method of claim 13 wherein the step of inserting the implantable lead is performed by:
- making a first incision, a second incision and a third incision;
- making a first tunnel between the first and second incisions;
- making a second tunnel between the second and third incisions; and
- passing at least the second end of the lead through the second incision to the third incision.

18. The method of claim 17 wherein the step of inserting the implantable lead is performed such that the retention device is accessible near the second incision, and the method further comprises using a suture to anchor the retention device to the patient at or near the second incision such that the first securing mechanism and the suture are both used to secure the lead in the selected position.

\* \* \* \* \*